United States Patent [19]

Ash

[11] Patent Number: 4,581,141

[45] Date of Patent: Apr. 8, 1986

[54] DIALYSIS MATERIAL AND METHOD FOR REMOVING UREMIC SUBSTANCES

[75] Inventor: Stephen R. Ash, Lafayette, Ind.

[73] Assignee: Purdue Research Foundation, West Lafayette, Ind.

[21] Appl. No.: 482,210

[22] Filed: Apr. 5, 1983

Related U.S. Application Data

[63] Continuation-in-part of Ser. No. 260,322, May 4, 1981, abandoned, and a continuation-in-part of Ser. No. 259,793, May 4, 1981, abandoned, which is a continuation-in-part of Ser. No. 104,016, Dec. 17, 1979, abandoned, which is a continuation-in-part of Ser. No. 881,684, Feb. 27, 1978, abandoned.

[51] Int. Cl.$^4$ .............................................. B01D 13/00
[52] U.S. Cl. .................................... 210/502; 210/648; 210/321.3
[58] Field of Search ............ 210/687, 648, 698, 321.1, 210/321.2, 321.3, 502; 252/180, 308, 316; 423/328, 327, 329

[56] References Cited

U.S. PATENT DOCUMENTS

| | | | |
|---|---|---|---|
| 1,365,760 | 1/1921 | Yoshizawa | 210/698 X |
| 1,571,891 | 2/1926 | Tellier | 210/687 |
| 3,608,729 | 9/1971 | Haselden | 210/321 |
| 3,742,946 | 7/1973 | Grossman | 210/321.3 X |
| 4,071,444 | 1/1978 | Ash et al. | 210/22 A |

FOREIGN PATENT DOCUMENTS

| | | |
|---|---|---|
| 874429 | 8/1979 | Belgium . |
| 790940 | 10/1980 | South Africa . |
| 1484642 | 9/1977 | United Kingdom . |
| 2014873 | 9/1979 | United Kingdom . |

OTHER PUBLICATIONS

Sherman, 10HSIV F-80 and 10HSIV W-85; Mol. Sieve Zeolite with Ion Exchangers for Removal of Urea Nitrogen, 1978.

Ash, et al., In-Vivo Evaluation of Ca-Loaded Zeolites and Urease for Urea Removal in Hemodialysis, 1980.

Primary Examiner—Frank Spear
Attorney, Agent, or Firm—Barnes & Thornburg

[57] ABSTRACT

Compositions for removing uremic substances during hemodialysis comprising an aqueous slurry containing charcoal, a highly calcium-loaded zeolite cation exchanger, purified urease (which may be bound to a portion of the zeolite, a suspending agent, and optionally an aliphatic carboxylic acid resin in the H+ form, and a hemodialysis method employing such compositions.

10 Claims, 10 Drawing Figures

DECREASE IN CREATININE CONCENTRATION WITH TIME, IN FLUID WITHIN BLOOD COMPARTMENT OF ARTIFICIAL KIDNEY. MORE RAPID DECREASE OCCURS WHEN SUSPENSION OF ABSORBENTS SURROUNDS MEMBRANES THAN WHEN WATER SURROUNDS MEMBRANES.

TITRATION OF ZEOLITES AND ZIRCONIUM PHOSPHATE WITH AMMONIUM CHLORIDE. AMOUNT OF AMMONIUM BOUND DETERMINED BY SUBTRACTION OF AMMONIUM CONTENT OF SUPERNATANT FROM AMOUNT ADDED TO THE SUSPENSION. AMMONIUM CONCENTRATION OF SUPERNATANT, AT EQUILIBRIUM, ON HORIZONTAL AXIS. ALL ZEOLITES ARE LOADED WITH SODIUM, ZIRCONIUM PHOSPHATE WITH HYDROGEN-SODIUM.

TITRATION OF ZEOLITES WITH AMMONIUM CHLORIDE AND AMMONIUM CARBONATE. AMOUNT OF AMMONIUM BOUND CALCULATED BY SUBTRACTION OF AMMONIUM CONTENT OF SUPERNATANT FROM AMOUNT ADDED TO SUSPENSION. AMMONIUM CONCENTRATION OF SUPERNATANT, AT EQUILIBRIUM, ON HORIZONTAL AXIS. ZEOLITES ARE 50% LOADED WITH CALCIUM.

BINDING OF AMMONIUM ON ZEOLITES FROM SOLUTION CONTAINING UREA AND UREASE. 30 MINUTES ALLOWED FOR UREASE REACTION TO REACH EQUILIBRIUM. SUPERNATANT CONCENTRATION OF UREA EXPRESSED AS AMMONIUM (2 AMMONIUM IONS DEVELOPED PER UREA MOLECULE).

EXPLODED VIEW OF A SMALL SECTION OF THE DIALYZER DESIGN 7

IN VIVO FRACTIONAL REMOVAL OF UREA FOR THE DIALYZERS 19A THROUGH 19E

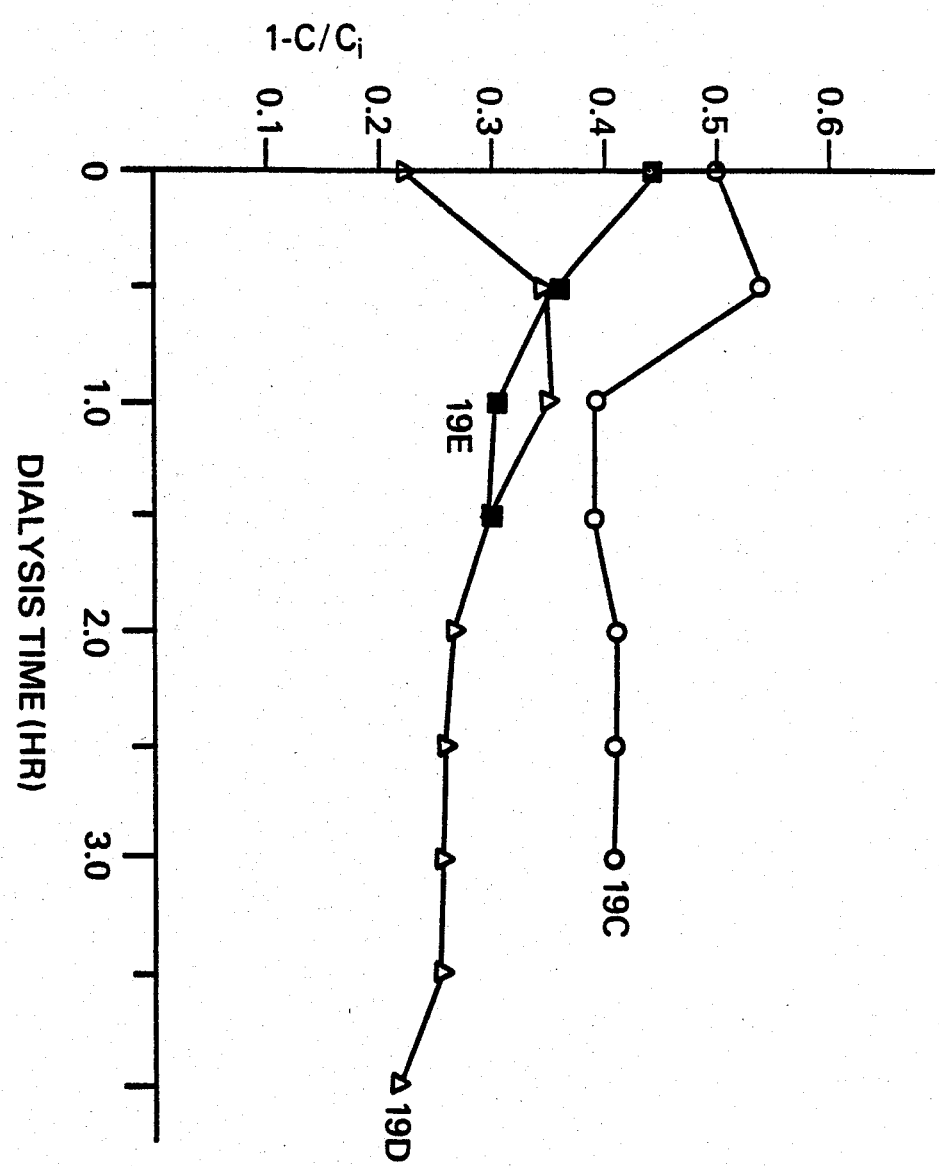

CONCENTRATION DIFFERENCE BETWEEN EFFLUENT AND INFLUENT BLOOD OF DIALYZERS 7B AND 7E (LOW CALCIUM LOADED ZEOLITE W 85 or F 80)

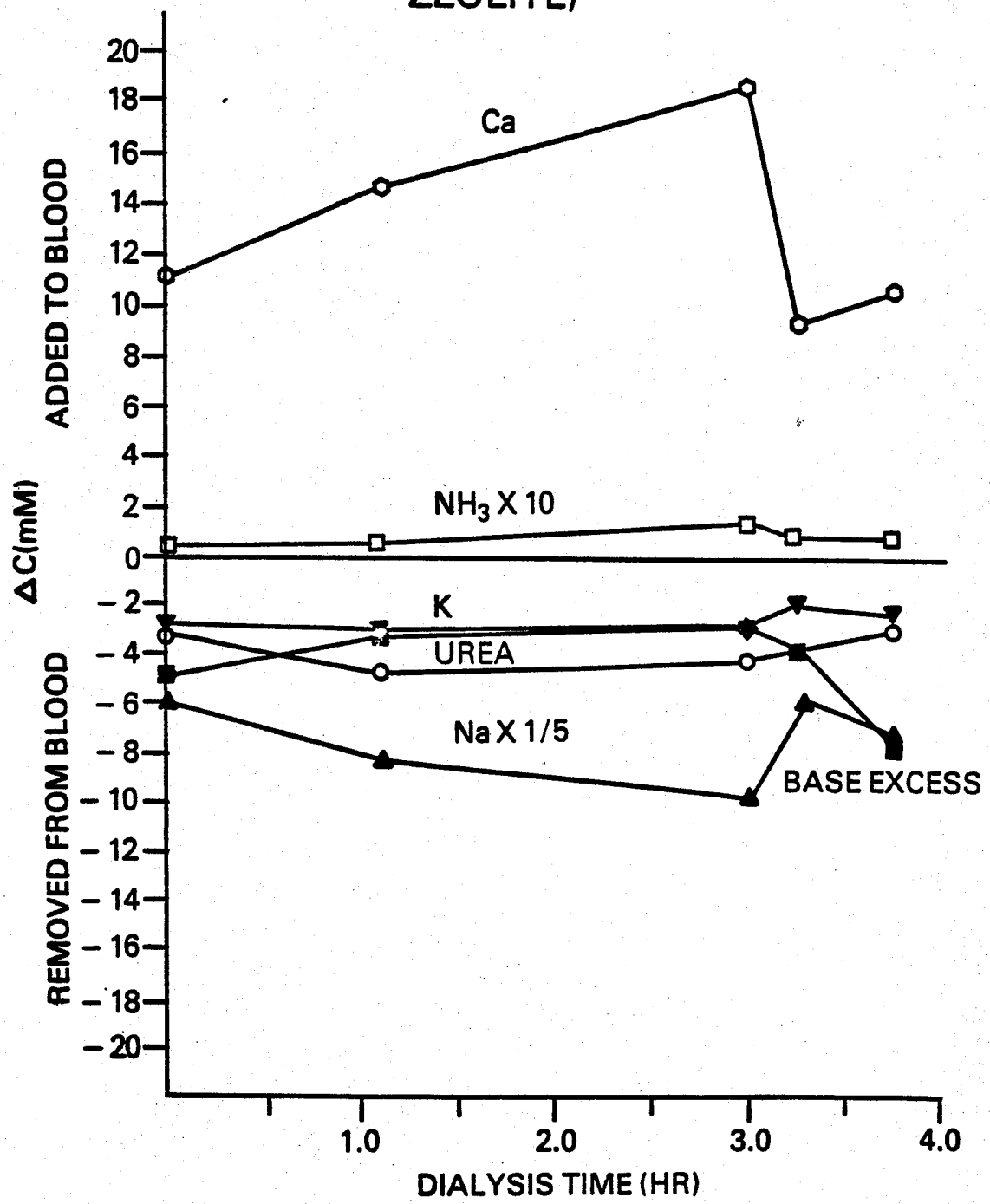

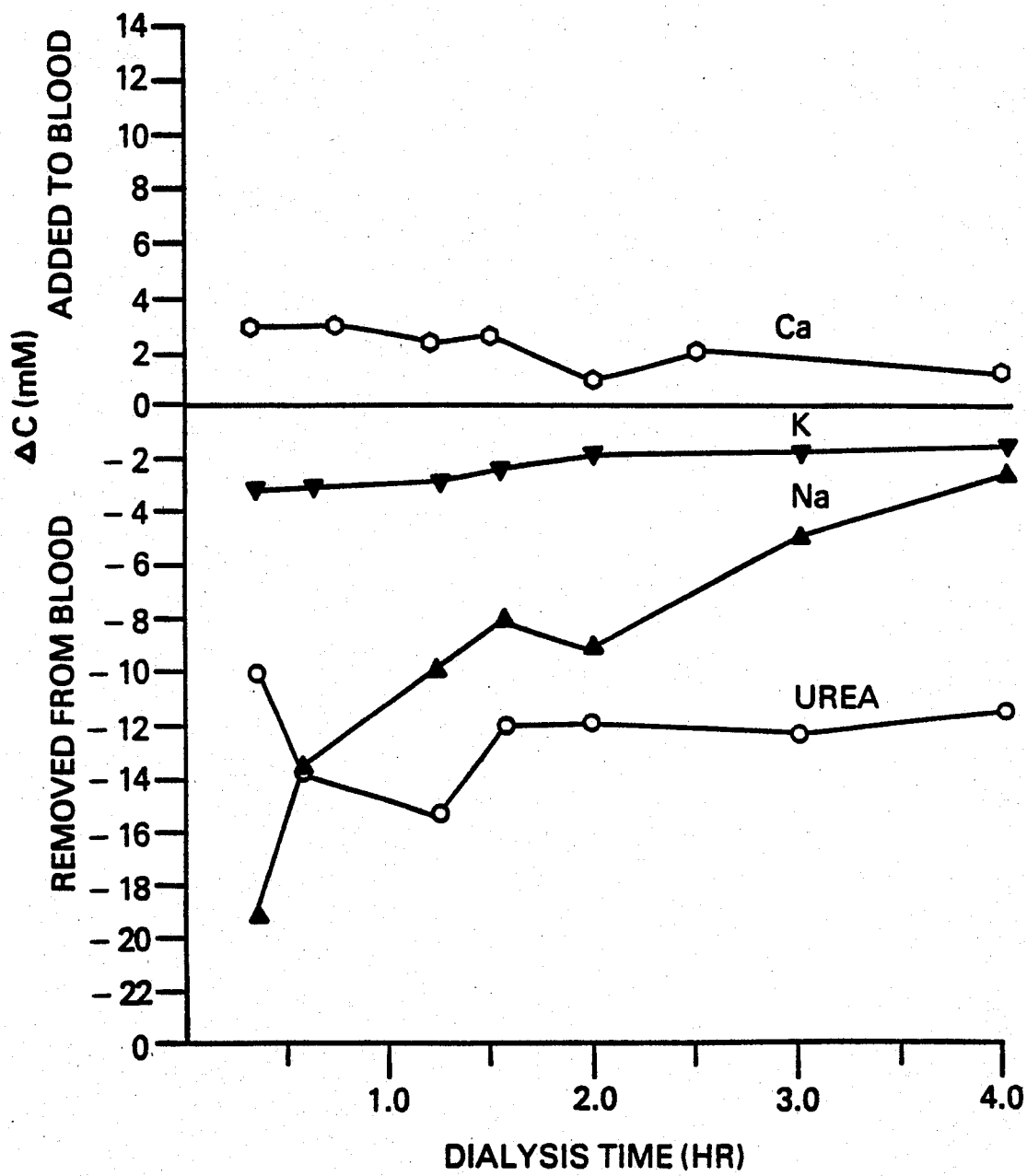

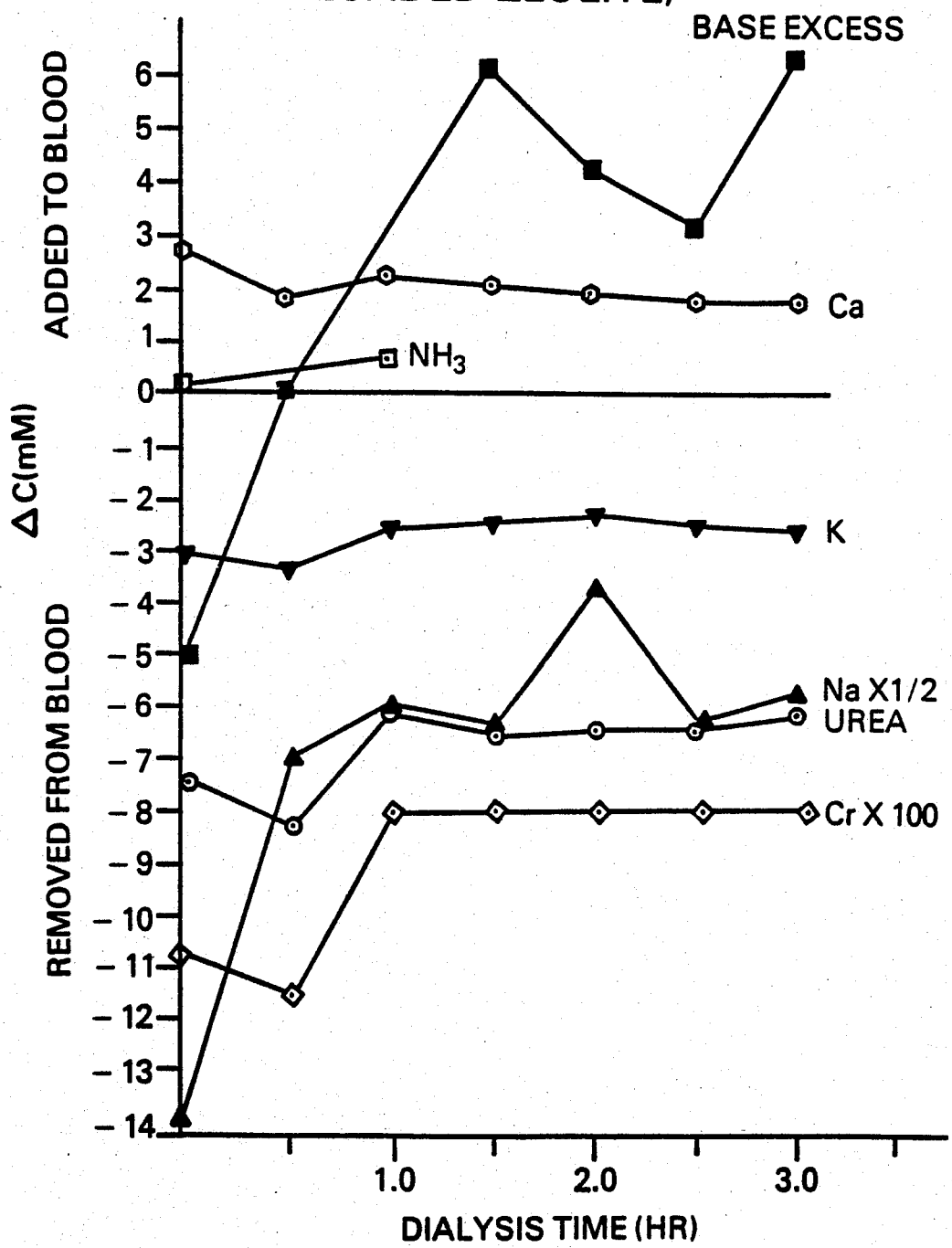

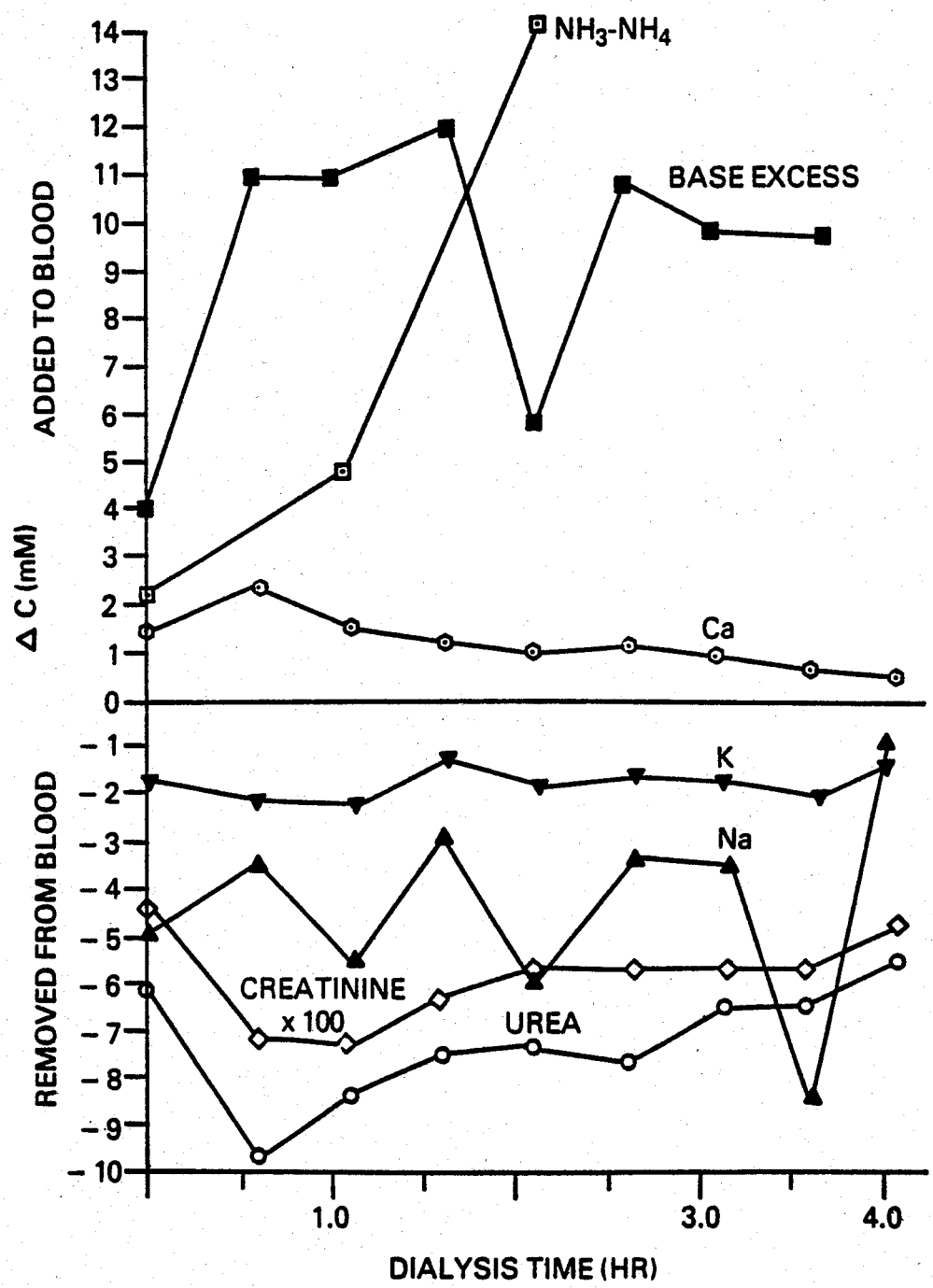

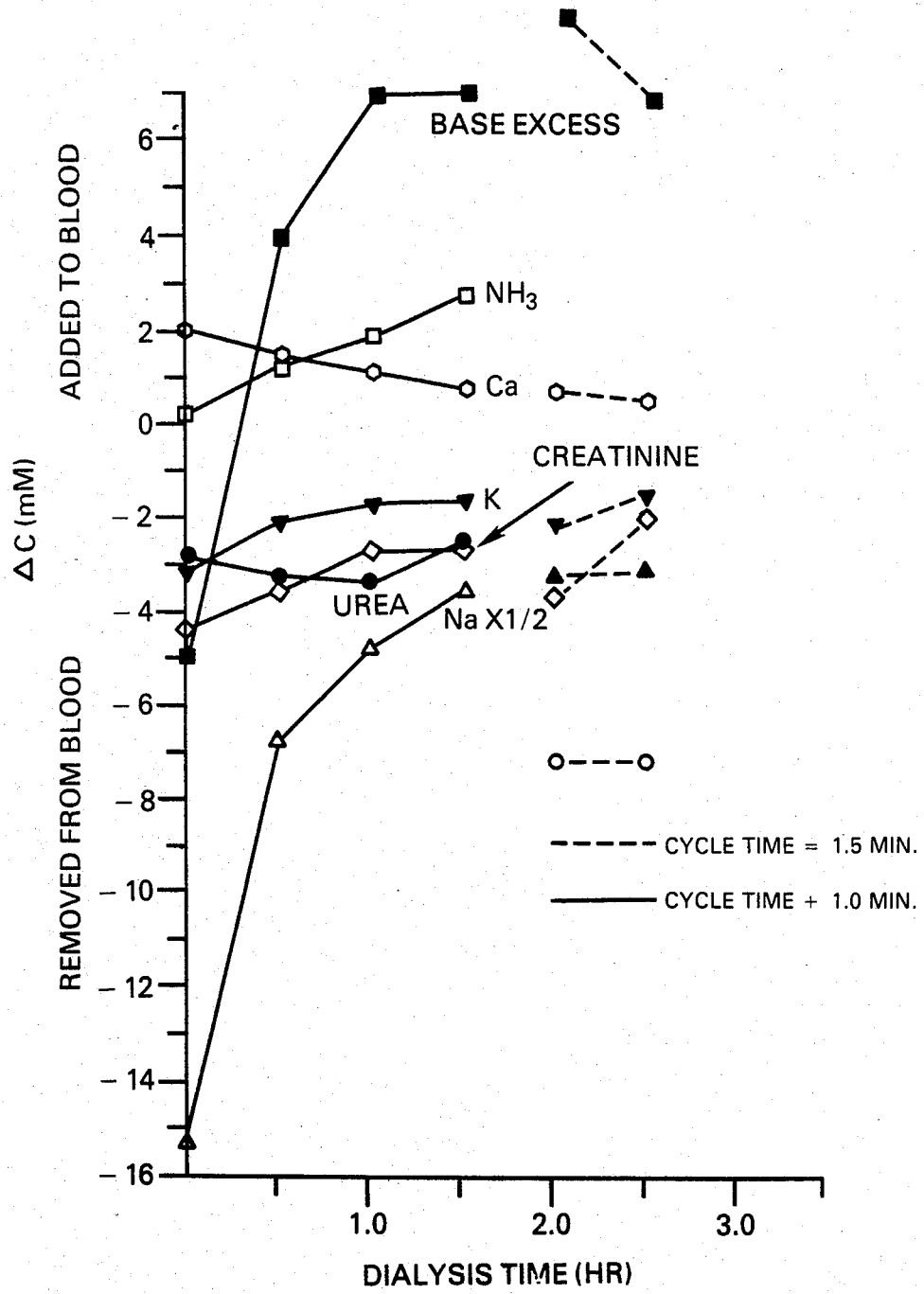

DIALYSIS MATERIAL AND METHOD FOR REMOVING UREMIC SUBSTANCES

This application is a double continuation-in-part of my U.S. patent application Ser. No. 259,793, filed May 4, 1981, now abandoned, and my U.S. patent application Ser. No. 260,322, filed May 4, 1981, now abandoned, which application was a continuation-in-part of Application Ser. No. 104,016, filed Dec. 17, 1979, now abandoned, which application was a continuation-in-part of my application Ser. No. 881,684, filed Feb. 27, 1978, now abandoned.

In mammals, when the kidneys fail to remove metabolic waste products from the body, most of the other organs of the body soon fail also. The totality of symptoms which ensue are termed uremia, and include bleeding, nausea and vomiting, cardiac arrhythmias, and coma. Death of the patient may result from a variety of these uremic complications. The severity of these symptoms is proportional to the retention in the blood of several known metabolic by-products ordinarily excreted by the kidneys. Two of the most toxic are urea and creatinine. Various other metabolic products which can accumulate in the bloodstream include polypeptides, phenols, guanidine, amines, and a variety of "middle molecules," in the molecular weight range 500–3000. The kidneys, when functioning normally, also provide electrolyte balance in the body, excreting $Na^+$, $K^+$, $H^+$, $Mg^+$, $PO_4^{-3}$, etc. ions in excess of body needs.

When partial or total kidney failure occurs, the above toxins will not be adequately excreted and the proper electrotype balance will not be maintained.

Uremia can be treated conservatively when renal failure is not too far advanced. As the chronic underlying renal disease progresses, however, recourse must be had to either a kidney transplant or to dialysis procedures. Dialysis is defined as the removal of substances from a liquid by diffusion across a semipermeable membrane into a second liquid. Dialysis of blood outside of the body (hemodialysis) is the basis of the "artifical kidney."

The artificial kidney treatment procedure generally used today is similar to that developed by Kolff in the early 1940's. In this procedure, blood is removed from the body, propelled through a closed system of membranes, and returned to the body, while on the other side of the membranes is a dialysis fluid, basically water. The membranes are semipermeable; that is, they allow small molecules to pass through, but retain larger molecules such as proteins, as well as cellular blood elements. Uremic substances, being small molecules, will pass through the membranes as long as the concentration of these substances is kept low in the dialysis fluid "dialysate" on the other side of the membranes. A dialysate volume of 120–200 liters is customarily used per dialysis treatment. Water so used must be prior treated to remove trace elements (which would otherwise pass back across the membrane into the blood), must be supplemented with electrolytes and glucose, and must then be warmed to blood temperature. The electrolytes are added to the dialysate so as to prevent excessive ion removal; i.e., $Mg^{++}$, $K^+$, $Na^+$, $Cl^-$, and $HCO_3^-$ (or a substrate buffer, acetate). $Ca^{++}$ should also be in slight excess so as to cause addition of calcium to the patient's blood, as the total body calcium in kidney failure patients is often low, leading to stimulation of parathyroid hormone, which is detrimental to the patient's health.

The artificial kidney has been the most effective of all artifical organs to date in terms of long-time support of patients. There are, however, certain problems inescapably associated with its use: the need for extensive training of patient and support personnel; trauma to vascular recesses during therapy; and development of adverse symptoms by the patient, including cramps, nausea, headache, and hypotension. In addition, the need for patient immobility is a further undesirable aspect of dialysis. The comparatively recent development of single-needle dialysis produces considerably less trauma to vascular access. Fewer adverse symptoms also may occur with appropriate choice of a dialysate buffer. Acetate, which is commonly used, has been shown to cause direct vasodilation, independent of pH effects, and with increased levels it is associated with several adverse symptoms, including "acetate intolerance." Bicarbonate-buffered dialysate produces considerably fewer adverse symptoms, especially in patients with an unstable cardiovascular system.

Present artificial kidneys require, in addition to a large volume of dialysate water, a rapid velocity of fluid on the dialysate side of the membranes to keep the concentration of uremic substances low immediately adjacent to the membrane. The rapid fluid velocity is usually accomplished by "recirculation" at a fast rate (such as 10 liters per minute) past the membranes of a "coil" dialyzer or by forcing dialysate through small channels of a "single-pass" dialyzer such as a hollow fiber or plate dialyzer.

In order for water to be withdrawn from the blood (another aspect of normal kidney action, it is necessary that pressure be higher on the blood side of the membranes than on the dialysate side, a positive pressure of 100–300 mm, Hg being ordinarily required. In "plate" or "hollow fiber" dialyzers, negative pressure is developed on the dialysate side to promote water removal.

A conventional artificial kidney machine must thus include: access to a large volume of pure water, a mechanism for addition of vital substances to the water, a blood pump, a dialysate pump, a membrane package, and a water heater. In addition, monitoring equipment must be available for blood and dialysate pressure, for dialysate temperature, and for concentration of electrolytes in the dialysate. The total amount of equipment is complex, expensive, and immobile. Artificial kidney machines are described in U.S. Pat. Nos. 3,352,422; 3,362,540; 3,570,672; 3,682,248 and in French Pat. No. 2,263,017.

One improvement in kidney machine operation has been to regenerate and recirculate the dialysate, thus permitting use of a smaller volume of water. Charcoal, urease, and an ion-exchanger, either zirconium phosphate or a natural or artificial zeolite, can be used for such regeneration purposes.

Charcoal is a non-specific adsorbent which has been shown to be a remarkably successful sorbent for a variety of uremic substances, having been shown to be effective in absorbing guanidines, creatinine, uric acid, and a variety of drugs as well as indicans, phenols, organic acids, and middle molecules. A major deficit in the functioning of charcoal is that it has only a small affinity for urea, and it removes essentially no water, phosphate, sodium, or other ions. Because of the deficiencies of charcoal, a complete sorbent-based dialyzer must include other sorbents.

The toxin which must be from the blood in largest amount is urea; 30 to 40 grams must be removed per dialysis on a three times per week schedule. Excretion of urea is the principal physiologic pathway for removal of nitrogen from the body. Urease has been often used to catalyze urea removal via hydrolysis according to the following equation:

$$2H_2O + H_4N_2CO \rightarrow 2NH_4^+ + CO_3^=.$$

For this reaction to be driven substantially to completion, $NH_4^+$ and $CO_3^=$(carbonate) must be removed. Some carbonate may be removed in an advantageous way be transfer to blood in the dialyzer if the urea hydrolysis takes place in proximity to blood-containing membranes.

Patients in renal failure are usually acidotic and are helped to maintain acid-base balance by carbonate which becomes bicarbonate under acid conditions. The total amount of bicarbonate produced from urea by urease would be in excess of that needed by the patient (200-250 meq per treatment). Therefore so control of the amount of bicarbonate returning to the blood is necessary, and further removal methods may be necessary, as described below. For significant and continued nitrogen removal from blood (and from the patient) by urease, an ammonium ($NH_4^+$) removal system, such as an ion exchange system, must be provided.

Ion exchanger systems which have been used successfully to remove $NH_4^+$ from dialysate include $Zr_3(PO_4)_4$ as a gel. The zirconium phosphate is prior-loaded with $H^+$ and $Na^+$, i.e., subjected to exchange of available cations with acid or an aqueous salt solution (NaCl). The ion exchanger and other components of the regenerative system are installed in a column through which dialysate is pumped, a urease layer being placed before the $Zr_3(PO_4)_4$ layer. Absorption of the $HN_4^+$ on the resin, replacing $Na^+$ or $H^+$, prevents re-entry of the $NH_4^+$ into the blood. $H^+$ released during $NH_4^+$ exchange is free to combine with $CO_3^=$ generated during the urease reaction to produce bicarbonate. The amount of $Na^+$ return requires dilution into the dialysate fluid.

A disadvantage of $Zr_3(PO_4)_4$ is its affinity for divalent ions including $Mg^{++}$ and $Ca^{++}$. Absorption of these ions decreases $NH_4^+$ pick-up, and depletes blood of these valuable ions. Reinfusion of $Mg^{++}$ or $Ca^{++}$ into the dialysate is thus necessary. In addition, the $H^+$ released during the $NH_4^+$ interchange exceeds the base ($OH^-$) generated and excess acidity results; therefore, acetate (or other) buffers must be utilized to correct the consequent acidosis of the patient. Additionally, since $Na^+$ is released during the ion exchange with $NH_4^+$, the initial $Na^+$ concentration in the dialysate must be lower than serum level. A relatively large volume of dialysate (5 liters) must be present, at about 100 mg percent starting $Na^+$ ion concentration. At the start of dialysis, therefore, there is a transfer of $Na^+$ from blood to dialysate while, at the end, there is a return of some $Na^+$ to blood. When $Na^+$ is depleted, there is a decrease in blood pressure, accentuating the hypotension which occurs during dialysis because of dilution and osmolality diminution at the beginning.

Other ion exchange materials then $Zr_3(PO_4)_4$ have been investigated for use with a urease-ion exchange system. One of the types of ion exchange materials studied has been the zeolites. Zeolites are crystalline, hydrated aluminum silicates containing various cations; these zeolites in general have excellent ammonium-binding affinities. The distribution coefficient for $NH_4^+$ vs. $Na^+$ has been reported to be 100 to 1 at $10^{-5}$ molar $NH_4^+$ for a typical zeolite.

Haselden U.S. Pat. No. 3,608,729 describes a portable hemodialysis apparatus for treating a stream of blood flowing on one side of a semipermeable membrane with adsorbent material on the other side, the adsorbent material being in the form of an immobile solid supporting the membrane, or an open work plastic grid packed with the solid adsorbent. The adsorbent included charcoal, anion-exchange resin, and urease.

Grossman U.S. Pat. No. 3,742,946 similarly describes only the use of solid adsorbents.

There are several disadvantages in using packed columns or layers of solid agents as set forth in the prior art for removal of impurities during dialysis. With sequential layering of absorbent compounds, favorable interactions of certain elements is impeded. Urease, for example, is inhibited by its own products, $NH_4^+$ and $CO_3^=$. Zirconium phosphate, which absorbs $Na^+$ and buffers $CO_3^=$, would not be present in the urease layer. As a result, large amounts of urease are needed to overcome by-product inhibition.

In addition, absorbent compounds must be carefully sized to prevent "packing" of the column by the dialysate flow—i.e., an increase of resistance when flow rates increase. A related problem is "channeling," or development of flow pathways which enable the dialysate to avoid much of the absorbent. As a consequence, the actual capacity of absorbent columns rarely equals that of the theoretical capacity of the absorbents present.

When absorbent materials are packed as an immobile solid next to dialysis membranes, the solid absorbent material packed closest to the dialysis membrane saturates rapidly with the particular substance to be absorbed, thus decreasing the efficiency of further removal of the substance. In such instances, time of diffusion through the absorbent may be the limiting factor in removing the substance, rather than concentration of the substance or relative affinity of absorbent for it.

Gambro U.S. Pat. No. 1,484,642 relates to the removal of toxins from the dialysis liquid in a recirculating dialysis system. Various zeolites are compared for their ability to remove $NH_4^+$ ions from a urea-containing dialysate which had previously contacted urease to produce the $NH_4^+$. In general, the zeolite employed is principally in the $Na^+$ form, but in order to avoid loss of $K^+$, $Ca^{++}$, or $Mg^{++}$ by absorption on the zeolite, the zeolite is preloaded with concentrations on $K^+$, $Ca^{++}$, and $Mg^{++}$ corresponding to their physiologic concentration. The concentrations of each ion in the dialysate and the ion affinity of the zeolite are both taken into account so that there is little net loss or gain of any given ion in the blood after completion of dialysis. The zeolite is placed in a column. The other materials, like urease bound to zeolite or carbon, are in separate columns; i.e., the materials used to remove toxins are separated geographically from one another and are in solid form.

Ash et al U.S. Pat. No. 4,071,444 discloses a reciprocating dialyzer using a sorbent suspension. The dialyzer contains a stack of resilient semipermeable membranes separated by gaskets and spacers which permit blood to be introduced through a central core bolt. This stack of resilient semipermeable membranes is placed inside a sealed container known as a dialysate chamber. The dialysate chamber contains as a sorbent mixture a combination of water-activated charcoal, zirconium phosphate, zirconium oxide, and urease.

To summarize, charcoal, urease, and zeolites particularly in the $Na^+$ or $H^+$ form are recorded as being useful sorbents for removing toxins in a recirculating or self-contained dialyzer, but always as immobile, packed solids bathed in a dialysate fluid. Nothing in the prior art hints at the use of a highly $Ca^{++}$-loaded zeolite not only to remove $NH_4^+$ from the dialysate but also to furnish $Ca^{++}$ ions to the dialysate, whereby $Ca^{++}$ ions can be returned to the blood stream, and excess carbonate urea can be precipitated. Thus, problems of excess bicarbonate absorption leading to acidosis can in large part be avoided.

It is therefore an object of this invention to provide a modified zeolite in which about 30 to 65% of the exchangeable sites are loaded with calcium ions, and further to provide an improved, simplified dialysis material.

It is another object of this invention to provide a novel suspended mixture of compounds useful as a dialysis material.

It is still another object of this invention to provide an improved dialysis material for removing uremic substances in an artificial kidney.

It is yet another object of this invention to provide a novel mixture of compounds, including a surface-absorptive agent, urease, an aqueous suspending medium, and a calcium-loaded cation exchanger in a particulate suspension, rather than in layers or in a column.

It is still another object of this invention to provide a novel suspended mixture of compounds that includes a calcium-loaded zeolite cation exchanger suspended in an aqueous suspending medium, which mixture returns a beneficial flux of electrolytes to the uremic patient.

It is still another object of this invention to provide sorbent compositions capable of varying the ion return so as to return the blood ion balances to normal in the uremic patient.

It is still another object of this invention to provide an improved dialysis material that requires no water bath, proportioning system, regenerating column, or reinfusion of electrolytes.

It is still another object of this invention to provide an improved method for removing uremic substances during hemodialysis.

It is still another object of this invention to provide an improved method for removing uremic substances during hemodialysis in an artificial kidney having membranes that includes providing a suspended mixture of compounds and contacting said membranes on one side with the suspended mixture of compounds.

It is still another object of this invention to provide an improved method for removing uremic substances during hemodialysis that requires no rapid movement of the dialysis material.

It is yet another object of this invention to remove uremic substances from the bloodstream while providing a beneficial return of ions to the blood from the dialysis material.

It is also an object of this invention to provide a dialysis method and a sorbent mixture suitable for use in a single-needle portable dialyzer by a majority of patients in kidney failure, with a concomitant lessening of expense plus simplification of the dialysis procedure.

It is a still further object of this invention to provide, in a recirculating dialysis apparatus, methods and compositions which remove uremic poisons from the blood while avoiding the introduction of excess $Na^+$ or $NH_4^+$ or depletion of $K^+$, $Mg^{++}$, or $Ca^{++}$.

Other objects of the invention will become apparent from the following description.

This invention provides a novel mixture of compounds useful as a dialysis material in treating blood to remove uremic substances (i.e., toxic substances that build up on kidney failure), as well as a novel method for removing uremic substances. The materials of this invention, when positioned in aqueous suspension contiguous to one side of the membranes of an artificial kidney, remove uremic substances from blood on the other side of said membranes without the necessity of use of a water bath, a proportioning system, or a regenerating column as now used in known artificial kidneys.

The dialysis mixture in a first embodiment comprises urease, preferably supported on a zeolite or other suitable material, activated charcoal, a highly $Ca^{++}$-loaded zeolite, and an aqueous suspending agent, said mixture becoming suspended on addition of the suspending agent so as to form a mobile phase prior to dialysis. In a second embodiment, the dialysis mixture comprises urease preferably supported on a zeolite or other suitable material, a highly $Ca^{++}$-loaded zeolite, an aqueous suspending agent, activated charcoal, and an aliphatic carboxylic acid resin in the $H^+$ form.

Additional features and advantages of the invention will become apparent to those skilled in the art upon consideration of the following detailed description of preferred embodiments exemplifying the best mode of carrying out the invention as presently perceived, which description should be considered in conjunction with the accompanying drawings, in which.

Figure 1:
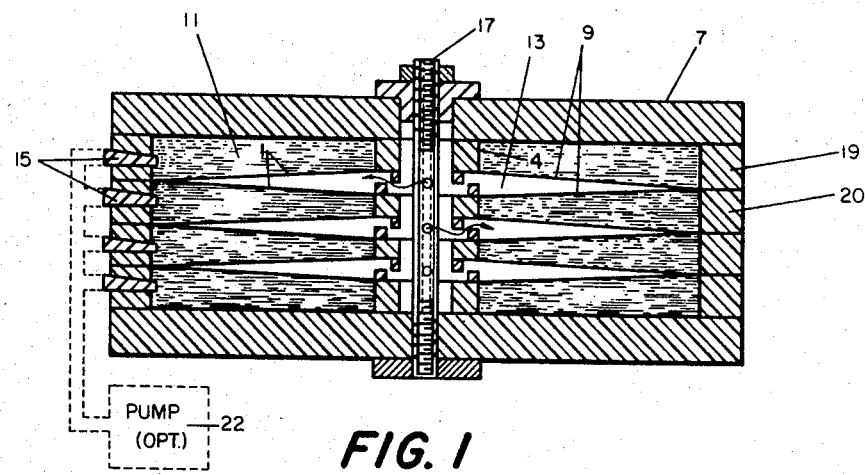
FIG. 1 is a cross-sectional view of artificial kidneys useful with the dialysis materials of this invention.

Referring now to drawings 1–6, an artificial kidney 7 is illustrated in cross-sectional view of FIG. 1. As shown, such an artificial kidney normally includes a plurality of semipermeable membranes 9 which are positioned so that dialysis material 11 (sorbent suspension) is on one side of the membrane and blood 13 is at the other side of the membrane. Suitable inlets 15 and 17 may be provided for the dialysis material and blood, respectively. In a flow-through system, suitable outlets (not shown) would likewise be provided as is well known to one skilled in the art. The membranes (which could also be shaped as hollow fibers, for example, rather than as shown) may be clamped between clamps 19 and 20 or otherwise secured. Artificial kidney machines are well known and such machines are shown, by way of example, in the patents referred to hereinabove. Such apparatus has therefore been illustrated herein only so far as is necessary to better explain the invention.

An artificial kidney having a single blood inlet and outlet aforementioned is described and claimed in U.S. Pat. No. 4,071,444, filed on Oct. 12, 1976, issued Jan. 31, 1978 to Stephen R. Ash, Philip G. Wilcox, and David P. Kessler. The novel compositions and methods of this invention are also useful in such a device, which device is included herein by reference.

In this invention, effective removal of uremic substances through semipermeable membranes 9 is performed by the placement of a suspension of absorbent compounds, made in accordance with the invention, on the dialysis side of the membranes. By locating the suspension of absorbent compound on the dialysis side of the membranes, the suspension can substitute for a high flow velocity dialysate fluid in a conventional artificial kidney and also substitute for the sorbent column used in the Redy ® regeneration of dialysis fluid or in the Gambro AG (loc. cit.). Mass transfer of uremic substances is very high in this method, as the diffusion distance for uremic substances on the dialysate side of the membrane is very small, and saturation of the sorbent immediately adjacent to the membrane is prevented by mixing of the sorbent suspension, thus constantly renewing the sorbent particles at the membrane surface.

The following substances have distinct advantages for use in such an absorbent suspension and have been utilized in various suspensions made in accordance with the present invention.

(a) charcoal, or other surface-adsorptive agents;
(b) zeolites, either naturally occurring or synthetic, highly loaded with calcium;
(c) urease in solution or suspension, or immobilized on particles, preferably by covalent bonding to the zeolite;
(d) an aqueous suspending agent, such as, for example only, water, or preferably water with methylcellulose, hydroxyethyl starch, or dextran; and
(e) an aliphatic carboxylic acid resin in the H+ form.

In selecting which substances to use in the sorbent suspension of the present invention, many factors were taken into consideration: (1) the ability of the substances to be effectively suspended; (2) the movability of the suspension; (3) the ion selectivity of the zeolites; (4) the production of beneficial by-products; (5) the loading of the zeolite; (6) the control of ion return to the blood so as to maintain or return the ion balance of the blood to normal; (7) assuring a beneficial flux of electrolytes to the blood; and (8) minimization of equipment necessary to perform the dialysis action.

It was found that by varying the composition of the suspension that this simple collection of sorbents, when combined in a suspension made in accordance with the invention, is capable of absorbing all uremic substances, and providing beneficial ion flux to the patient. Because the suspension is mobile, it circulates fast enough to prevent saturation of the absorbents near the membrane surface. This motion may be produced by membrane motion in the dialyzer packages (as indicated by the dotted pump insertion in FIG. 1). In a hollow fiber configuration (not shown) with all of the absorbents near a cellophane surface, it may be possible to effect dialysis with minimal movement of the sorbent suspension.

While the zeolites that were utilized in the sorbent suspensions made in accordance with the invention were Linde F-80, Linde W-85, phillipsite, and clinoptilolite, many other zeolite materials could be used. Alternate catalysts besides urease for urea destruction also could be used. Charcoal can be replaced in the suspension by other surface active materials. Two or more cation exchangers could be added, as in embodiment 2, and one of several other suspending agents also could be utilized. The effectiveness of using a "slurry" or suspension of the aforementioned substances is shown by the more effective removal of uremic substances by an artificial kidney when a suspension made in accordance with the invention is utilized rather than water.

Figure 2:
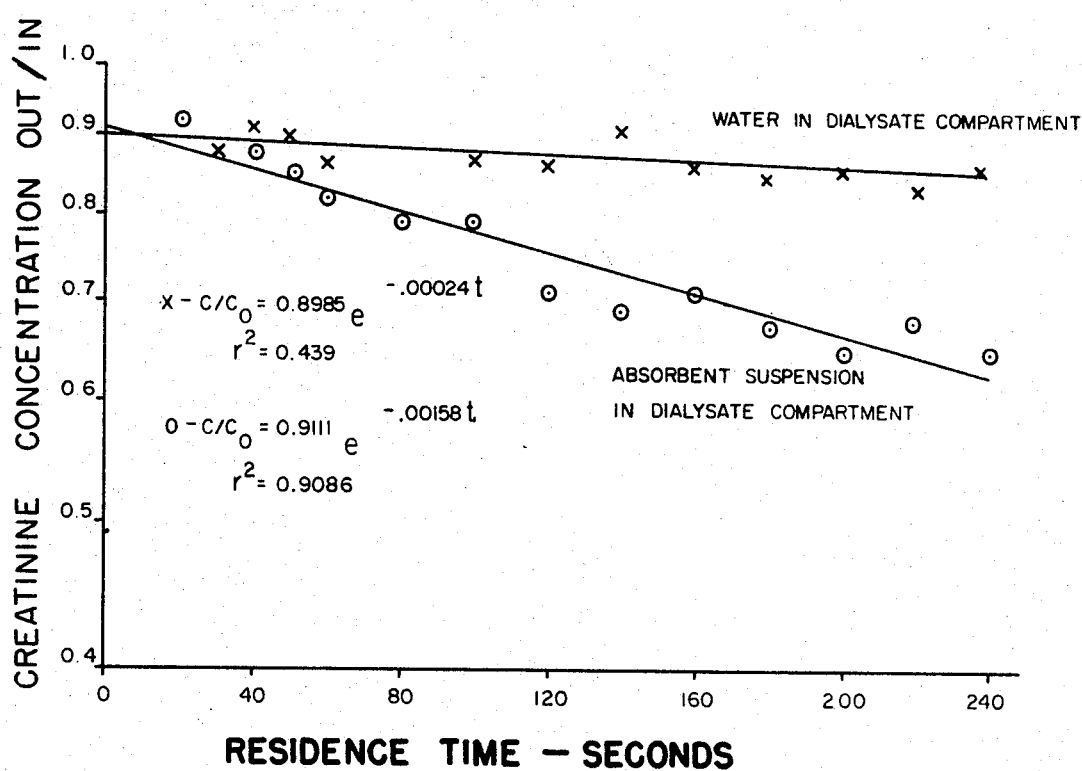
FIGS. 2–5 are graphs illustrating the invention.

Referring to FIG. 2, the time course of removal of one uremic substance, creatinine, through cellulose membranes is shown. The vertical axis is the ratio of creatinine concentration in fluid leaving the membrane packages to the entering concentration. This membrane package utilizes an "in and out" flow of fluid, and therefore, the time of residence of the creatinine solution in the packages is expressed in "cycle time." It is apparent that a much more effective removal of creatinine occurred when membranes were surrounded by a "slurry" or suspension of absorbing compounds made in accordance with the invention, than when the membranes were surrounded by water. Even when water flow was very high in this dialyzer membrane package, the effectiveness of removal of creatinine (mass transfer coefficient) did not reach that found when a suspension was utilized.

Zeolites were chosen over other cation exchangers since the selectivity of zeolites for ammonium is significantly higher than that of most other cation exchange materials. Additionally, the total (maximal) content of exchangeable cations is higher in zeolites (7 meq/g for Linde F-80, according to Union Carbide technical data, vs. 2.0 meq/g for zirconium phosphate, according to CCI data). As a result, the removal of ammonium is higher with a zeolite as the supernatant ammonium concentration is increased.

Figure 3:
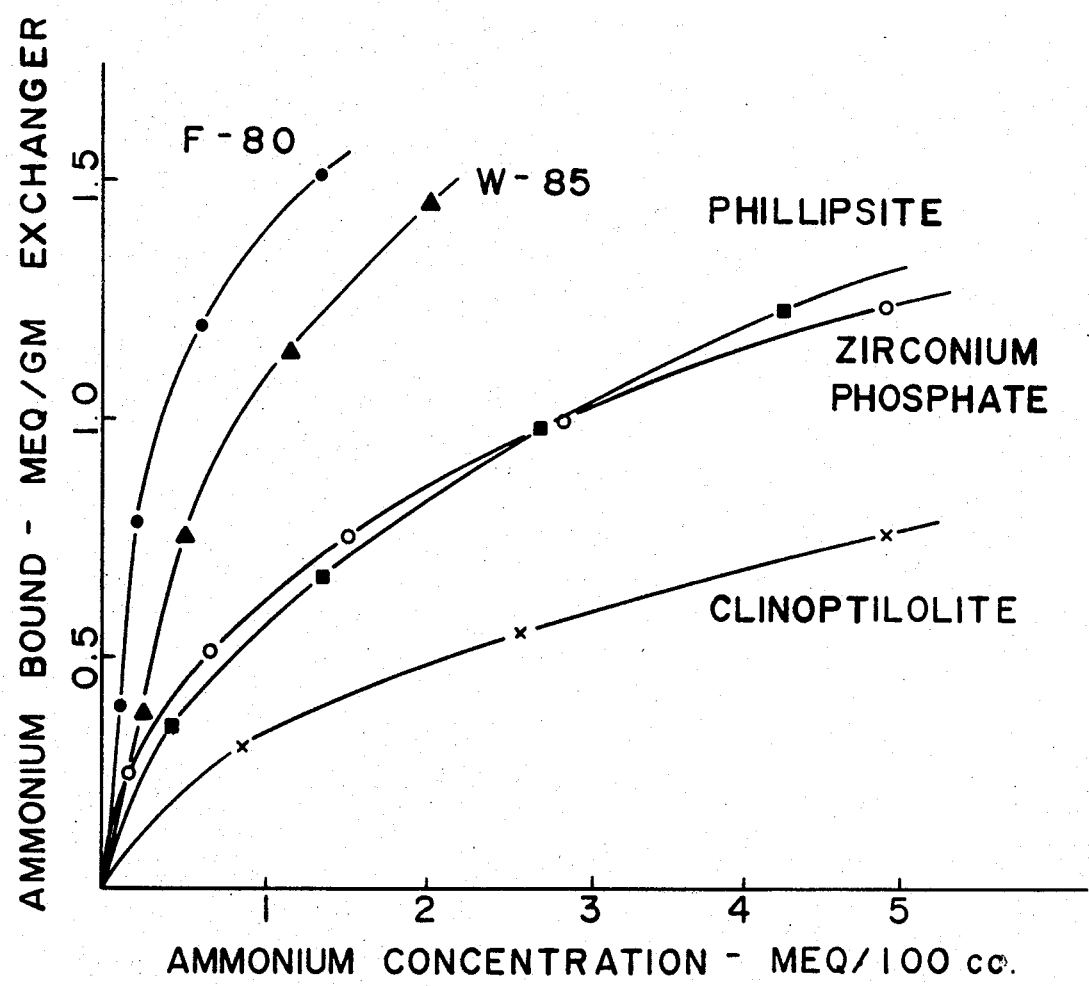

FIG. 3 indicates the amount of ammonium bound on various cation exchangers during titration of a suspension of these exchangers with $NH_4Cl$. All of the exchangers are $Na^+$ loaded, with the exception of zirconium phosphate, which is $H^+$-$Na^+$ loaded. As was indicated, Linde F-80 and W-85 bind approximately twice the $NH_4^+$, at a low concentration of $NH_4^+$, as zirconium phosphate or phillipsite. Zeolite binds approximately 4 times the $NH_4^+$ of clinoptilolite, at each $NH_4^+$ concentration.

Figure 4:
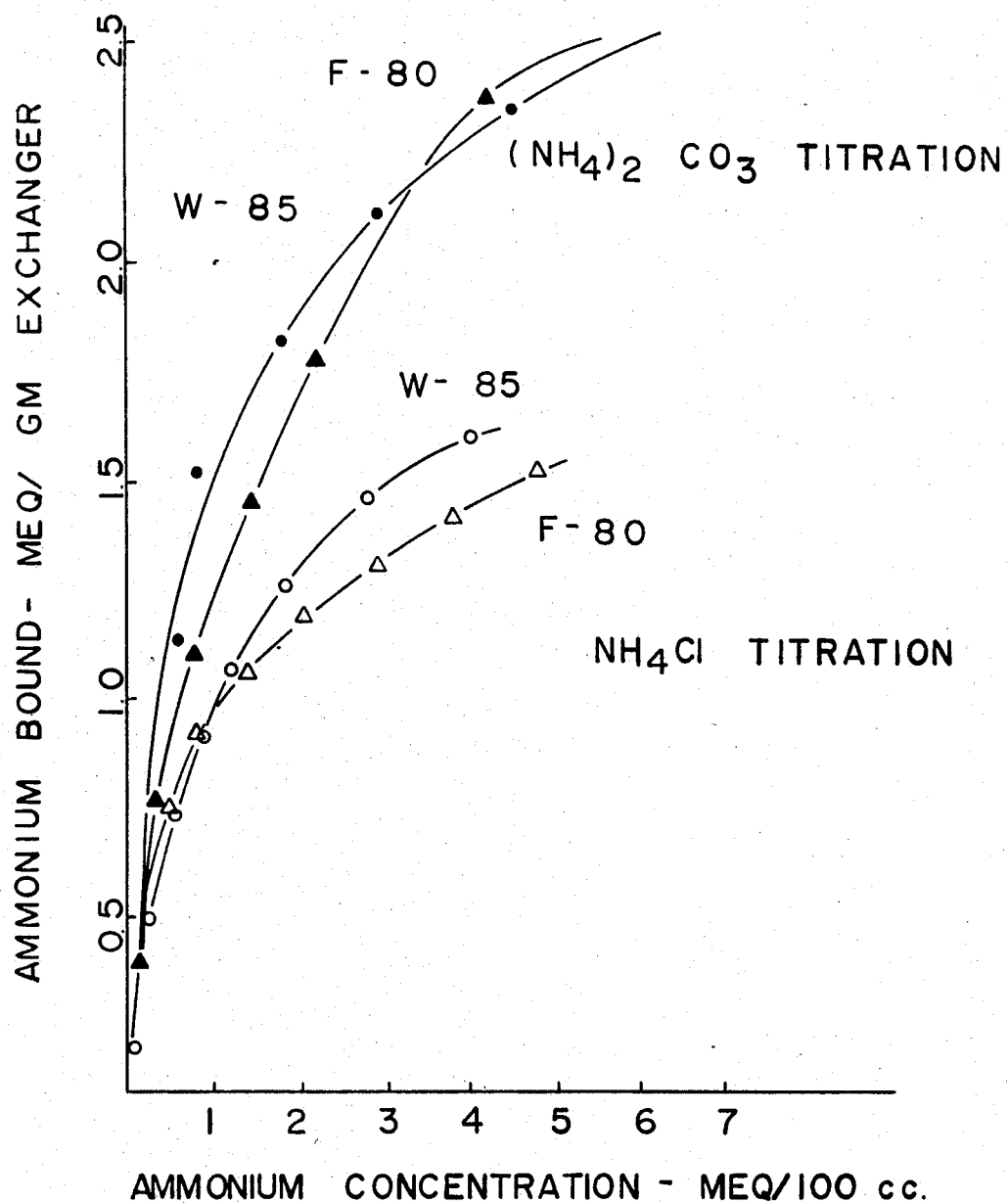

This selectivity is due to the fact that the crystalline framework of zeolite cation exchangers tends to exclude ions with certain sizes and charge densities. As a result, zeolite materials are among the few cation exchange materials which have a higher selectivity for ammonium than for divalent cations such as calcium. This property allows the loading of zeolites with calcium ions and subsequent exchange with ammonium ions which facilitates controlling ion return in the suspension and creating a beneficial flux of ions back to a patient. FIG. 4 indicates the binding of ammonium on zeolites Linde F-80 and W-85, after calcium loading of these materials (30% calcium with the remainder sodium or potassium). Methods of loading the zeolites are discussed hereinafter. The lower curve indicates titration of the zeolites with $NH_4Cl$. Comparison with a similar curve in FIG. 3 indicates that the binding of ammonium is only slightly decreased by calcium loading of zeolites vs. sodium loading of zeolites. In contrast, the loading of zirconium phosphate with calcium ions allows almost no exchange of ammonium ions for calcium ions, owing to a high selectivity of zirconium phosphate for calcium ions.

FIG. 4 also indicates the titration of zeolites Linde F-80 and W-85 with ammonium carbonate. As indicated, the binding of ammonium at the higher pH level of ammonium carbonate solution is significantly greater than the binding at the lower pH level during ammonium chloride titration. Since the hydrolysis of urea by urease produces ammonium carbonate, the titration of zeolite with ammonium carbonate should predict the binding of ammonium in the presence of urea and urease.

Figure 5:
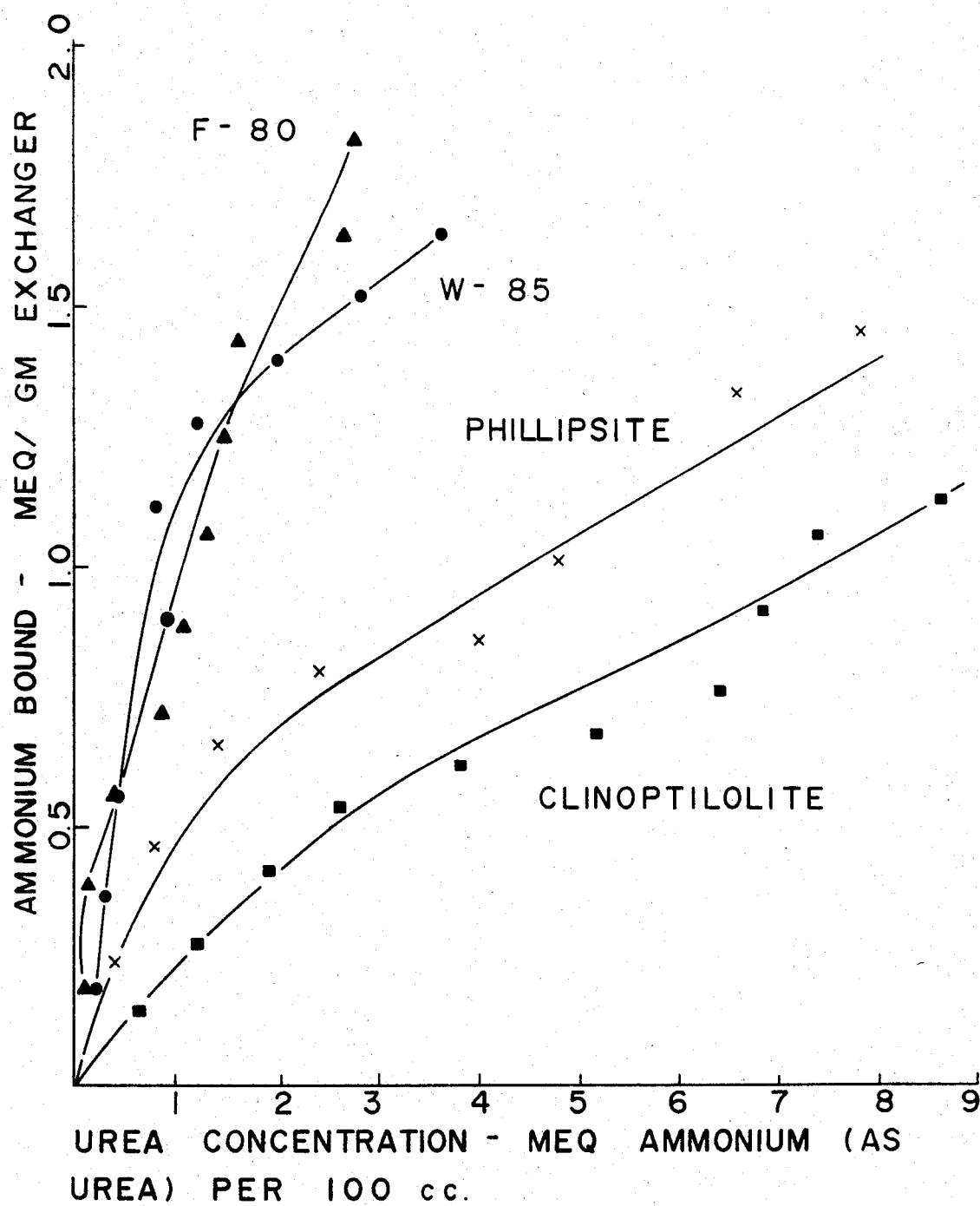

Because zeolites have selectivities which allow exchange of ammonium ions for calcium ions, and because optimal binding occurs at high pH levels, calcium-loaded zeolites remove the nitrogen produced by urea degradation extremely well. FIG. 5 indicates the ammonium binding on low calcium-loaded zeolites after addition of urea to the supernatant. The zeolite is approximately 20% $Ca^{++}$ loaded by twice suspending the zeolite in 0.4M $CaCl_2$, twice centrifuging, and resuspending in water. Urease is present in low concentration, 0.5 g. or 200 Sumner units per 100 cc., and 30 minutes is allowed for completion of the reaction. The results indicate that the binding of ammonium is approximately the same as for titration of zeolites with ammonium carbonate; at a concentration of 0.2 meq. ammonium (from urea) per 100 cc in the supernatant, 1.4 meq. ammonium is bound per gram of F-80 or W-85 (low calcium-loaded). Higher loading of $Ca^{++}$ onto the zeolite can be achieved by higher $Ca^{++}$ concentrations during zeolite synthesis. Testing of these highly loaded (50%) zeolites is set forth below.

In order to assure an effective transfer of uremic substances across the dialysis membranes of a dialyzer utilizing the sorbents of the present invention, it is important to remove urea at a rate which exceeds the transfer of urea across the membranes. Thus, the equilibrium ammonium binding of zeolite is not as relevant as rapidity of binding during the urease reaction. In the presence of 10 g. of cation exchanger per 100 cc, urease operates at a maximal velocity equivalent to the Sumner units of the urease (manufacturer's assay of maximal activity). Excess urease (5 g/100 cc) and increased time allows binding of urea nitrogen (ammonium) similar to equilibrium binding (FIG. 5) in two minutes.

Additionally, zeolites were chosen for the further reason that the density of zeolite materials is much less than that for zirconium phosphate (specific gravity of 2.5). This permits greater ease of suspension, important for the maintenance of absorbing compounds near the surface of membranes. In a solution of 0.5% methylcellulose, having a viscosity of 1500 centipoise, all the zeolites tested have been suspended almost indefinitely (Linde F-80, Linde W-85, phillipsite, and clinoptilolite). These zeolite suspensions are also persistent after the addition of charcoal and urease. In contrast, a zirconium phosphate gel (CCI life systems) remains suspended only 10 minutes in this concentration of methylcellulose.

It is also readily apparent that the particle size of the sorbent is important in maintaining an effective sorbent suspension. Smaller particle sizes yield a better suspension and overall efficiency is increased by increasing the surface area of the sorbents and by minimizing the diffusion distances required for the uremic substances to reach or penetrate the sorbent particles, i.e., such as the time required for an $NH_4^+$ ion to find a site on the zeolite carrying $Ca^{++}$ or $Na^+$, or for a urea molecule to encounter a coupled urease molecule. It has been found, however, that further pulverizing of the commercially available zeolites utilized in the dialysis compositions made in accordance with the present invention can lead to undesired effects, such as aggregation.

The commercially available zeolites utilized in the sorbent suspensions of the current invention are composed of particles 1-10 microns in diameter and varying in shape from roughly spherical to cuboidal. To measure the propensity of a resin or zeolite of particular size to aggregate, the following equation involving rate of flow can be utilized: $T = V_m$, wherein T is time and V is volume as measured in a gravity flow meter (see Barile et al, AICHE Abstracts-Chicago Meeting Nov. 16-20, 1980). The exponent "m" is determined empirically, and is always greater than one, but for present purposes should be as close to one as possible. Determinations of "m" have been useful in establishing which sorbent slurries will not aggregate in a four-hour period, that period being the estimated time for daily dialysis utilizing solvent suspensions made in accordance with the current invention.

Suspension of absorbents allows the dialysate to be kept in juxtaposition to the dialysis membranes without the rapid flow rate of the dialysate common to ordinary artificial kidneys. A slow flow or movement at the membrane surface of the suspension is sufficient to prevent absorbents at the membrane surface from becoming saturated with uremic substances from the blood. In the single-needle device, shown in U.S. Pat. No. 4,071,444, movement of the membranes, due to blood compartment volume change, is adequate to circulate the mobile sorbent suspension and prevent saturation.

As FIGS. 2-4 indicate, zeolites loaded with calcium can effectively remove ammonium during the urease reaction. Clearly, however, zeolites loaded with sodium, as depicted in FIG. 3, would seem to work equally well. Nevertheless, several distinct advantages attend the use of calcium-loaded zeolite materials in the suspension. These advantages make the use of this particular urease-ion exchange system highly desirable:

(1) Calcium ions are released when ammonium ions are absorbed and some of these calcium ions return to the patient through the dialysis membranes. Calcium ions are beneficial to the patient, as they replace the depleted body stores of calcium, and decrease the level of parathyroid hormone, usually high in dialysis patients. Calcium is one of the few cations not toxic to a patient in kidney failure. Sodium, hydrogen, potassium, and magnesium are all potentially toxic.

(2) $CO_3^=$ is a product of the degradation of urea by urease. This carbonate is not neutralized by $H^+$ on the cation exchange material (as with $H^+$-$Na^+$ loaded zirconium phosphate or zeolite). Therefore, some of this $CO_3^=$ is free to return to the patient. As patients with kidney failure are acidotic, $CO_3^=$ is beneficial to the patients in moderate quantities, for example, allowing more deposition of calcium. Parathyroid hormone is also decreased if acidosis is corrected.

(3) Neither $Ca^{++}$ nor $CO_3^=$ is returned to the patient in great excess, or in amounts equal to the amount of $NH_4^+$ removed. During dialysis, calcium carbonate is formed and precipitates on the dialysis side of the membrane when its solubility product is exceeded. This precipitation prevents passage through dialysis membranes into the bloodstream of the patient of that quantity of $Ca^{++}$ and carbonate precipitated. During in vitro tests of the urease reaction in the presence of calcium-loaded zeolites, the calcium in the supernatant actually falls. For example, the binding of 2 meq/g. of ammonium ions during this reaction is asociated with a fall in supernatant calcium ions from 27 mM/l. to 1 mM/l. This is caused by the precipitation of calcium carbonate.

Bicarbonate returned to the patient is also reduced by this precipitation. If 18 grams of urea are produced by a patient daily, for example, 18 grams (or 300 mM.) must be removed by dialysis to prevent uremic poisoning. This amount of urea is equivalent to 600 meq of ammonium ion generated during the urease reaction. The return of 600 meq of calcium or 600 meq of $CO_3^=$ to the patient would be excessive. Precipitation of calcium and bicarbonate in the form of calcium carbonate according to the process of this invention successfully limits the return of these substances to the patient via the dialysis membrane.

(4) Calcium ions freed by reaction of the zeolite with $NH_4^+$ react with phosphate to form a calcium phosphate precipitate on the dialysis side of the membrane. Since phosphate must also be removed during the dialysis procedure, this precipitation is another benefit of the novel process utilized by the present invention, since it results in a decrease in blood phosphate levels. A specific phosphate binder, zirconium oxide for example, is therefore not necessary. Experiments with a uremic dog have indicated that the phosphate removal through a membrane package was such that the phosphate blood concentration dropped 50% between in-flow and out-flow blood. This drop was approximatley the same percentage drop in concentration as for creatinine, urea, or potassium.

(5) Sodium loading or hydrogen loading of zeolites results in return to the patient of sodium or hydrogen, both of which are toxic substances in renal failure. Re-infusion of base (usually acetate buffer) is necessary to counterbalance this return of $H^+$. For example, 5 liters of fluid with a low sodium concentration is necessary for dilution of sodium released in some prior-art systems. Use of highly calcium-loaded zeolites as in the current invention eliminates the necessity for re-infusion of base or the use of large dialysate volumes.

(6) In most cases, only one ion exchange material is necessary, in comparison to two in other prior art recirculatory systems. Thus, the weight and bulk of absorbents are decreased.

When the absorbent compounds are placed next to the dialysis membranes in suspension, as in the process of this invention, then the distance necessary for diffusion of uremic substances is small before removal from solution. Excellent mass transfer occurs across the membranes because the absorbent keeps the uremic substances in low concentration in the dialysis compartment. Thus, a suspension of absorbing compounds, as used in this invention, has good effectiveness even at slow flow of the suspension, and its effectiveness at slow flow is better than that of water at high flow velocity.

The placement of a suspension of absorbing compounds next to dialysis membranes rather than in columns geographically removed therefrom allows elimination of several components of standard dialysis machines such as the large water requirement, the mixture of ions and glucose with the water, water treatment, water-heating systems, and high water velocity near the membranes (produced by narrow-flow dialysate channels or a high-flow recirculating pump).

In addition, the suspension of absorbents has advantages over the use of absorbents in a column; fluid channeling is avoided and space requirements for the sorbent are minimized. Furthermore, pumps and water connections from the dialysis membranes to the column are, of course, not needed. In addition, only a slow movement of absorbing compounds in suspension is necessary to prevent saturation of absorbent compounds near the membranes.

In summary, placement of a suspension of absorbents, made in accordance with the present invention, next to the membranes of an artificial kidney offers the advantage of making the dialysis equipment simpler, and of increasing mass transfer of the uremic substances through the membranes. Zeolite materials, a component of the absorbent mixture, are well suited to the absorption of ammonium ions, produced by the urease reaction. The loading of such zeolite materials with calcium results in beneficial calcium and carbonate fluxes to the patient. The calcium thus produced also limits the return of phosphate to the patient. The fluxes of calcium and carbonate are less than the flux of urea out of the patient, because of precipitation of calcium phosphate and calcium carbonate in the dialysis chamber. Sodium, acetate, and hydrogen overloading of the patient is avoided, a major problem with other regenerative systems. $Ca^{++}$ and $Mg^{++}$ depletion is also avoided. Suspension of the absorbents makes for a mobile dialysis phase which mixes as the reciprocating membrane activated by the pump pushes blood into the dialyzer or removes it, thus avoiding saturation of the dialysate sorbent materials and channeling of the dialysate flow in the sorbents.

EXAMPLE 1

Figure 6:
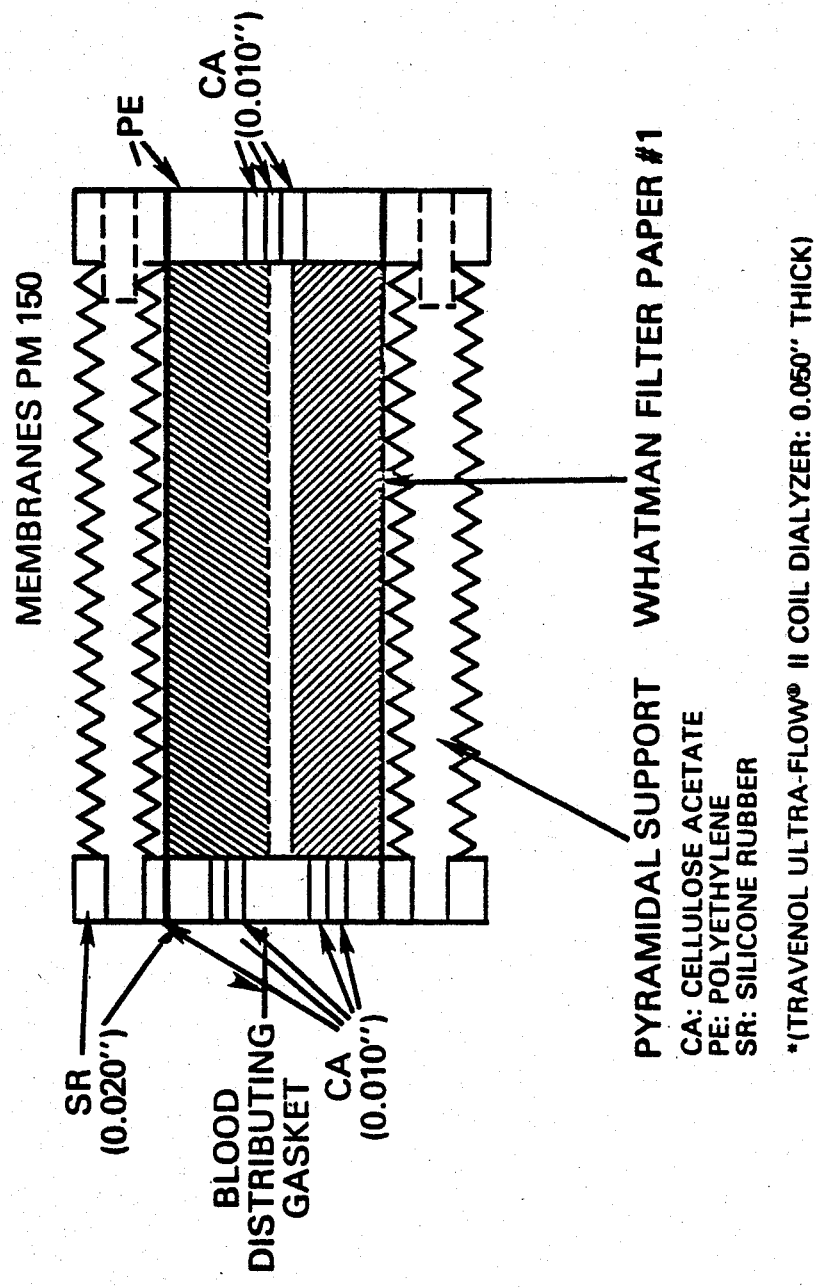
FIG. 6 is a cross-sectional view of artificial kidneys useful with the dialysis materials of this invention.
Figure 7:
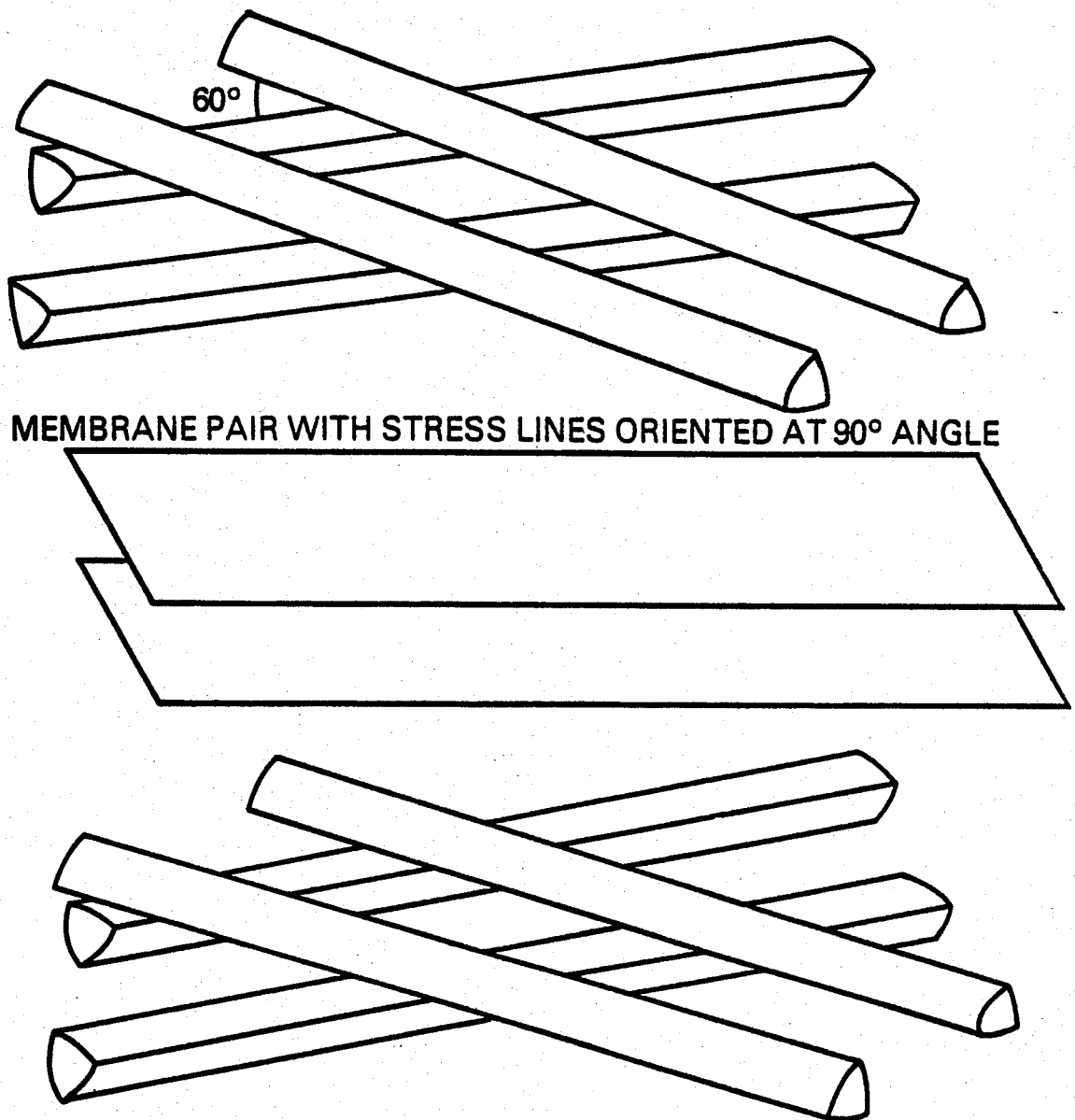
FIG. 7 is an exploded view of one such artificial kidney useful with the dialysis materials of this invention.

An in vivo test of a first embodiment of the novel dialysate compositions and dialysis method of the present invention was carried out as follows: The dialyzer employed, illustrated in FIG. 6, is of the type described in U.S. Pat. No. 4,061,444. Each dialyzer unit had from 8 to 19 membrane packages, which were 5 inches in diameter. Each package consisted of a pair of Cuprophan membranes (PM150) and a center gasket 0.75 inch in diameter and 0.04 inch in thickness. The center gaskets allowed blood to flow between the membrane pairs. Each membrane pair was enclosed between two nylon screens. The periphery of each package was sealed by two cellulose acetate rings. Each screen was 4.5 inches in diameter and had an 0.8 inch diameter hole in the center. The screen consisted of two superimposed layers of parallel strands. The parallel strands of these two layers were at a 60° angle. The details of the screen are shown in FIG. 7. The void space of each screen was filled with about 11 grams of sorbent paste. The detail of the sorbent mixture is described below. The sorbent screens were allowed to air dry at room temperature for two to three hours before assembling. The membrane stress lines (lines of contraction upon wetting) were oriented perpendicular to the screen strands facing the membrane (except in 19A in which they were at 45° angles). The stress lines of each membrane pair were also oriented perpendicular to each other. A small (0.010 inch) space was left between the two support screens so that most of the blood flowing into the membrane package would expand the membranes into spaces between the parallel strands. The above arrangement was chosen to minimize the membrane distension upon filling and to facilitate complete draining of blood during the half cycle of outflow. Dialyzer model 19 had a larger (⅜ inch) hole cut in the Whatman filter paper, referred to below, and an extra cellulose acetate gasket filling this hole.

The sorbents in each screen were constrained between the membrane and a piece of filter paper (Whatman No. 1). This filter paper allowed transport of water out of the sorbent suspension and thus allowed the opening and closing of the membrane package. Each filter paper was supported on an injection-molded polyethylene support with numerous 0.020 inch by 0.020 inch pyramidal projections. This pyramidal support had notches on the periphery for water exit from the sorbents.

After assembling eight to nineteen packages along with their screen suports, filter papers, and pyramidal supports, the unit was then clamped between two aluminum plates utilizing six stainless steel threaded rods on the outer edge. The unit was pressure sealed by tightening the nuts on the threaded rods.

After sealing, the unit was then pressure tested at 300 mm Hg. An air-tight coupling was placed between the blood inlet port and a mercury manometer. The rate of fall of the mercury column indicated the rate of air transfer across the membrane packages. Adequate sealing was indicated by a fall of the column from 300 to 290 mm Hg in 10 seconds or longer. If adequately sealed, the unit was then placed inside a plexiglass case. Sodium chloride or sodium bicarbonate solution was added to the case. The unit was then ready for the mechanical test mentioned below.

Water was usually added prior to use to place the sorbents in suspension.

Zeolite—Low Ca-Loaded

The zeolites used were prepared as follows: F-80 and W-85 zeolites were obtained from Union Carbide Corp. The materials, when obtained, were primarily sodium-loaded, although some potassium was present. A 5% suspension in 0.5 molar aqueous calcium chloride solution (200 grams zeolite per 4 liters solution) was prepared. After approximately 1 hour of thorough mixing, the zeolite was allowed to settle, and the supernatant decanted. The zeolite was then filtered and dried. When resuspended in 0.7% sodium chloride, this mixture had the following equilibrium concentrations: 150 meq per liter of sodium, and 3 to 15 meq per liter of calcium. (Approximately 1.5 meq per liter of calcium was bound per gram zeolite.)

Zeolite W-85—Very Highly Ca-Loaded

The W-85 zeolite was prepared in the presence of calcium, and was found to have 4.5 mg exchangeable calcium per gram. At equilibrium in mixture with water, glucose, and charcoal, the calcium level was 122 ppm, Na level 1 meq for this zeolite.

Zeolite W-85—Highly Ca-Loaded

Initial tests with dialyzer 19(a) (highly calcium-loaded) indicated an excessive amount of calcium-sodium exchange utilizing this very highly calcium-loaded zeolite. Such zeolites contain about 4.5 meq/g $Ca^{++}$ and about 1.5 meq/g $Na^+$. Thereafter, Ca-loading was decreased by contact with 0.4% NaCl, then with $NaHCO_3$. The $HCO_3^-$ served to limit the equilibrium calcium level by precipitation. The $Na^+$, $K^+$, and $Ca^{+2}$ equilibrium levels after each loading were as follows:

| First loading: | 400 g high-calcium zeolite was added to 0.4 g % NaCl solution to 4 liters. The supernatant concentration was as follows: | | | |
|---|---|---|---|---|
| | Na (meq/l) | K (meq/l) | Ca (meq/l) | pH |
| | 15–18 | 0–0.02 | 53 | 7.8–7.9 |
| Second loading: | Zeolite was added to 3.6 liters $NaHCO_3$ solution containing 2 meq $NaHCO_3$ per gram of zeolite. The supernatant concentration was as follows: | | | |
| | Na (meq/l) | K (meq/l) | Ca (meq/l) | pH |
| | 99–103 | 0 | 3.1–4 | 7–7.1 |

During the first loading, approximately 0.5 meq Na was loaded onto each gram of zeolite. In the second loading, 1.1 meq Na was loaded. Therefore, the exchangeable sites of the modified high-calcium zeolite were one-third sodium and two-thirds calcium.

Instead of titrating a very highly $Ca^{++}$-loaded zeolite (about 66% $Ca^{++}$) with a solution of sodium salt to obtain a zeolite having about 50-50 $Ca^{++}$-$Na^+$ loading, a mixture of a very highly $Ca^{++}$-loaded zeolite and a sodium or sodium-potassium-loaded zeolite in about a 2 to 1 ratio can be employed. The final zeolite mixture will average about 40–50% replaceable $Ca^{++}$ ions. Whether a single zeolite or a zeolite mixture is employed, the zeolite should contain, per gram, 2.8–3.2 meg $Ca^{++}$ (preferably about 3.0 meq $Ca^{++}$) 2.3–3.0 meg $Na^+$ (preferably about 2.5 meq $Na^+$) and from 0 to 1 meq $K^+$ (preferably about 0.5 meq $K^+$). A small amount of zeolite, either the calcium-loaded or the sodium-potassium-loaded form, will have urease covalently bound to it.

Activated Charcoal

Powdered charcoal USP was obtained from Mallinckrodt Inc. This charcoal had been shown in vitro to adequately bind creatinine, uric acid, and other organic materials at low concentrations.

Zirconium Phosphate

Zirconium phosphate used was similar to that of the Redy ® system. It was obtained from CCI Life Systems (Oklahoma City, Okla.), a division of Organon Tecknikon. The zirconium phosphate was loaded partially with sodium and partially with hydrogen.

Urease Bound to Zeolite F-80 or W-85

Samples of W-85 and F-80 were first loaded with calcium or sodium solution as mentioned above, and were then ready for binding to urease. Standard methods of binding can be used—see Iyengar and Rao, *Biotech. and Bioeng.*, 21, 1333 (1979). A preferred method of binding urease to a zeolite is as follows:

500 g. of calcium-exchanged Ionsiv w (a zeolite obtained from Union Carbide) were ground in a mortar and then dried at 55° C. for about 48 hours. The ground zeolite was suspended in 2000 ml. of a 12% (v/v) solution of gamma-aminopropyltriethoxysilane in toluene. The reaction mixture was stirred overnight at about 95° C. and was then filtered through Whatman No. 1 paper. The filtered zeolite was washed three times by suspending the filter cake in 500 ml. of toluene, slurrying, and then refiltering. The filtered zeolite was washed twice more in the same manner with 500 ml. of acetone, except that the filter cake was collected on Whatman No. 4 paper. Next, the filter cake was washed three times in the same way with 900 ml. of a 0.05M sodium bicarbonate solution containing 0.001M calcium chloride using Whatman No. 4 paper. The washed zeolite was then suspended in 1 liter of the same bicarbonate-calcium chloride solution and held overnight at 4° C. Next, an additional 6.5 liters of the above bicarbonate-calcium chloride solution was added to the slurry. Sufficient glutaraldehyde was added to give a final concentration of 2.5% (v/v). The reaction mixture was stirred at ambient temperature for about three hours and the derivatized zeolite was separated by filtration on Whatman No. 1 paper. The filter cake was washed five times by suspension in 900 ml. of the same bicarbonate-calcium chloride solution and then refiltered using Whatman No. 4 paper. A Tollens test for aldehyde showed faintly positive. Next, crude urease was dissolved in 2000 ml. of the same bicarbonate-calcium chloride solution in sufficient quantity to give a 10 mg./ml. concentration. The urease solution was filtered through a Cuno Zeta+ filter. The washed zeolite obtained as above was suspended in this solution and the resulting mixture stirred for two hours at ambient temperature. The mixture was then kept at 4° C. overnight. The zeolite-containing urease bound thereto was recovered by filtration on Whatman No. 1 paper and was washed five times with 900 ml. of the same bicarbonate-calcium chloride solution by the process previously outlined, and the zeolite was recovered by filtration on Whatman No. 4 paper. The Tollens aldehyde test was negative after the second wash. After the final wash, the wet urease-zeolite was suspended in sufficient volume of the same bicarbonate-calcium chloride solution to give a final total volume of 1400 ml. The suspension had the following characteristics: Total solids, 0.3313 g./ml., urease activity, 110 $\mu$/ml.; total units of urease activity bound to zeolite equals 67% of total starting units.

The zeolite having urease bound thereto was recovered by filtration and dried. Total yield=4.638 g.

Urease is bound to zeolites F-80 and W-55, phillipsite, or clinoptilite in the calcium-loaded form by the same procedure. In such case, the urease-bound calcium-loaded zeolite is substituted for part of the total calcium-loaded zeolite needed.

The zeolite having urease bound thereto was then washed thoroughly with distilled water, and the urease activity of the zeolite particles was determined. Activity ranged from 90 to 120 international units per gram of zeolite (measured at BUN of 90 to 100 milligrams percent).

Urease before binding to a zeolite must be solubilized, and toxic components minimized. One way of purifying urease is as follows: Jack bean meal is extracted with water (400 g. with 20 liters of glass-distilled water). The mixture is stirred at room temperature for thirty minutes, and then centrifuged at 10,000×g for thirty minutes at 4° C. The supernatant is freeze-dried in stainless steel pans in the vacuum oven at 30° C. The yield of crude urease from this amount of meal is approximately 100 g. with a specific activity of approximately 30 $\mu$/mg of protein. The average yield of enzyme is about 3300 units/gram of meal.

Next, 30 g. of crude urease is dissolved in 3.0 liters of sterile, pH 7 phosphate buffer containing 0.1M NaCl and 0.001M Na$_2$EDTA. The cloudy solution is clarified by pressure filtration through a Cuno Zeta+ filter cartridge. In addition to clarifying the solution, this filter medium also removes some of the endotoxins present in the crude extract. This solution is then stirred for 90 minutes at room temperature with 50. g dry weight equivalent of activated thiol-Sepharose 4B which had been previously swollen and equilibrated with the same buffer. Activated thiol-Sepharose 4B is a mixed disulfide formed between 2,2'-dipyridyl disulfide and glutathione coupled to CNBr-activated Sepharose 4B. After binding the urease, the mixture is filtered under suction on a medium porosity sintered glass funnel. The Sepharose is then washed in place on the funnel by resuspending three times in 250 ml of the pH 7 buffer. It is then equilibrated with sterile pH 8, 0.1M phosphate buffer containing 0.1M NaCl and 0.001M Na$_2$EDTA. A total of approximately 1.0 l. of the buffer is used in multiple washes to effect the equilibration. The urease is then eluted by stirring with 360 ml. of the pH 8 buffer made 0.025 molar in L-cysteine at room temperature for 30 minutes. The resulting mixture is filtered on a sintered glass funnel, and the elution repeated a total of five times. The first three eluates contain 96–98% of the total elutable urease, and they are added to a final concentration of 0.1 mg/ml to help stabilize the urease. This solution is then dialyzed in Visking tubing for twenty hours, with stirring, at 4° C. against 25 volumes of 0.1M NaCl to remove the cysteine, cystine, and most of the phosphate. The final dialyzed eluate is then used as the source of urease in the slurry for the self-contained artificial kidney or for binding to a zeolite.

The sorbent mixture used in exemplifying the sorbent suspension and method of the present invention was prepared for use as follows: the charcoal powder was mixed in a 1 to 3 (weight to weight) ratio with the $Ca^{++}$-loaded zeolite and urease-bound zeolite. For each gram of this dry mixture, about 1.7 ml of water were added to yield a thick paste. The paste was spread onto the screen with a spatula. Table 1 indicates the sorbent compositions of the three dialyzers reported here. For dialyzers which did not have urease bound to zeolites (7B and 7D), purified soluble urease was added after assembling the membrane packages. Reciprocating motion of the membrane pairs allowed the soluble urease to connect and diffuse to the vicinity of the membranes.

The suspending agent is added to the dry mixture in such an amount that the concentration during dialysis will be about 0.5% for methoxycellulose. Alternatively, a 0.5% solution of methoxycellulose (1500 centipoises) can be added to the above dry mixture to yield a suspension of zeolite and charcoal and the dialysate suspension placed in the dialyzer in the necessary amount.

The sorbent systems of Table 1 were partially dried into the interstices of the dialyzer screen supports. The suspension properties after re-wetting could not be verified, and some saturation of the zeolite may have been observed. In the Table, the term "mod. Ca" means about 40% calcium loading of zeolite (high $Ca^{+2}$) zeolite equilibrated with $Na^+$.

For the purpose of testing numerous chemical fluxes during dialysis, it was decided to test a number of various dialyzers on a partially anephric animal (a healthy mongrel dog weighing 26 kg in which renal insufficiency had been created by total removal of one kidney and ligation of one of two arteries to the other kidney). Prior to the removal of the kidney and ligation of one of the two arteries, an arterio-venous shunt was constructed.

Following surgery, the blood urea nitrogen and creatinine were measured daily for one week, and then approximately 3 times weekly after that. The BUN rose to 60 and creatinine to approximately 3.5, at which point they both stabilized. Electrolytes were normal. The arterio-venous shunt was replaced after three weeks due to clotting. The venous cannula was replaced with a 1/16 inch inner diameter silicone tube with three side holes. The silicone tube was placed in the superior vena cava. The subcutaneous tract and cuff were similar to the venous cannula used in the arterio-venous shunt. The venous cannula was filled with 3 cc heparin (the fill-volume of the cannula itself) daily. No other care was performed for the cannula.

Performance of Dailysis Procedure In Vivo

The dialyzer was sterilized by placing approximately 50 cc of Betadine ® in the dialyzer for 10 minutes and then removing the Betadine ® by syringe. Several syringes of normal saline (sterile irrigation fluid) were then injected and withdrawn from the dialyzer in order to remove $I_2$. The process was continued until the iodine color (light yellow) cleared.

After sterilization, approximately 50 cc. of normal saline were placed in the dialyzer. The dialyzer was then hooked up to the graduated cylinder reservoir. Means for varying the pressure, maintaining sterile conditions, and removing blood samples were provided. The dialyzer was then connected using a multiple connection to the arterio-venous shunt of the dog. Shunt pressure and mean arterial pressure were measured and recorded. Pulse rate was also noted from the arterial pressure tracing. Temperature was recorded on the animal, general physical condition, and capillary refill time. The dialysis was then begun by turning on the timer and vacuum pump and cycling the pressure in the dialyzer case.

Once every half hour, inflow and outflow chemical determinations were made during the dialysis, using appropriate techniques for removing blood from the dog (usually through a rubber port). Assays were done each half hour for calcium, sodium, potassium, pH, $P_{CO_2}$, creatinine, BUN, and ammonium ion. The BUN and creatinine were assayed as mentioned above; sodium and potassium assays were performed on a flame spectrophotometer, calcium on an atomic absorption unit, and ammonium ion by the glutamine synthetase method. Base excess was calculated by standard formulas from $P_{CO_2}$ and pH of blood.

General clinical conditions, blood pressure, pulse rate, and temperature were recorded on the dog at least every half hour during the experiment. No changes in any of these parameters were seen except for occasional sinus bradycardia and tachycardia (also recorded during control sessions without dialysis).

During dialysis of the dog, body temperature, blood pressure, and general appearance did not change. In two dogs prepared as above, the pulse did tend to vary from bradycardia (40 to 50) to tachycardia (180). The dogs were not sedated and evidences of tachycardia occurred whenever a strange person or sight would appear.

The experimental conditions are listed in the attached Table 1.

Figure 8A:
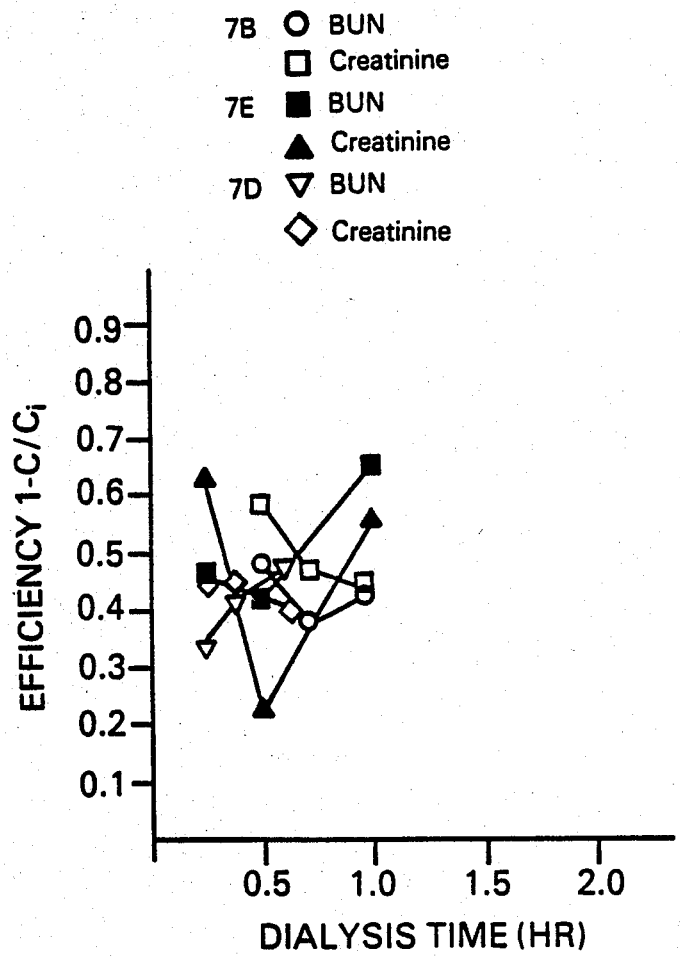
FIGS. 8–10 are graphs illustrating the invention.

Inflow-outflow measurements for various solutes in the blood were determined as discussed in the above method. Urea removal is indicated in FIG. 8a, as is creatinine removal. Fractional removal was approximately 40 to 60%. The fractional removal did not significantly change with time, thus indicating a lack of sorbent saturation for either urea or creatinine during the test. Blood flow rate into the dialyzer was somewhat variable. However, each dialyzer had a maximum fill volume of approximately 2 to 3 ml per membrane package (1 to 1½ ml per 100 cm² surface area).

TABLE 1

DESCRIPTION OF DIALYZERS AND EXPERIMENTAL PARAMETERS IN EXAMPLE 1

| Dialyzer No. | Total Membrane Area (meter²) | Sorbent Systems | | | | | Flow Conditions | | | |
|---|---|---|---|---|---|---|---|---|---|---|
| | | Zeolite | | Charcoal | Urease | | Inflow Vacuum Time | | Outflow Pressure Time | |
| | | Type | % | % | Type | IU/ml | (mmHg) | (sec) | (mmHg) | (sec) |
| 7B | 0.38 | W85 | 33 | 11 | S | 80 | 200 | 60 | 100 | 30.60 |
| 7D | 0.16 | ZP | 41 | 14 | S | 62 | 200 | 36 | 100 | 36 |
| 7E | 0.28 | F80 | 50 | 17 | Z.B. | 4.5 | 200 | 48 | 100 | 12 |
| 19A | 0.40 | 111Ca | 46 | 15 | S | 4.5 | 100 150 200 250 | 48 | 100 | 12 |
| 19B | 0.32 | Mod. Ca | 56 | 0 | S | 80 | 200 | 42 | 100 | 18 |
| 19C | 0.40 | Mod. Ca | 40 | 16 | S | 80 | 200 | 42 | 100 | 18 |
| 19D | 0.30 | Mod. Ca | 54 | 10 | Z.B. | 70 | 200 300 400 | 42 | 100 | 18 |
| 19E | 0.30 | 1 part Mod. Ca with bound urease + 5 parts Mod. Ca | 114 | | Z.B. | 24* | 200 | 42 | 100 | 18 |

| Dialyzer No. | Dog Renal Status | Blood Access | Dialysate Solution |
|---|---|---|---|
| 7B | ⅔ nephrectomy | AV shunt | 0.7% NaCl |
| 7D | Normal | AV shunt | 0.7% NaCl |
| 7E | ⅔ nephrectomy | venous catheter | 0.7% NaCl |
| 19A | ⅔ nephrectomy | venous catheter | 4% glucose |
| 19B | ⅔ nephrectomy | venous catheter | 40% mM NaHCO₃ 3% glucose |
| 19C | ⅔ nephrectomy | venous catheter | 40 mM NaHCO₃ |

TABLE 1-continued
DESCRIPTION OF DIALYZERS AND EXPERIMENTAL PARAMETERS IN EXAMPLE 1

| | | | | |
|---|---|---|---|---|
| | 19D | ⅔ nephrectomy | venous catheter | 40 mM NaHCO$_3$ |
| | 19E | Normal with urea infusion of 0.5 g/Kg body wt. | venous catheter | 40 mM NaHCO$_3$ |

Figure 8B:
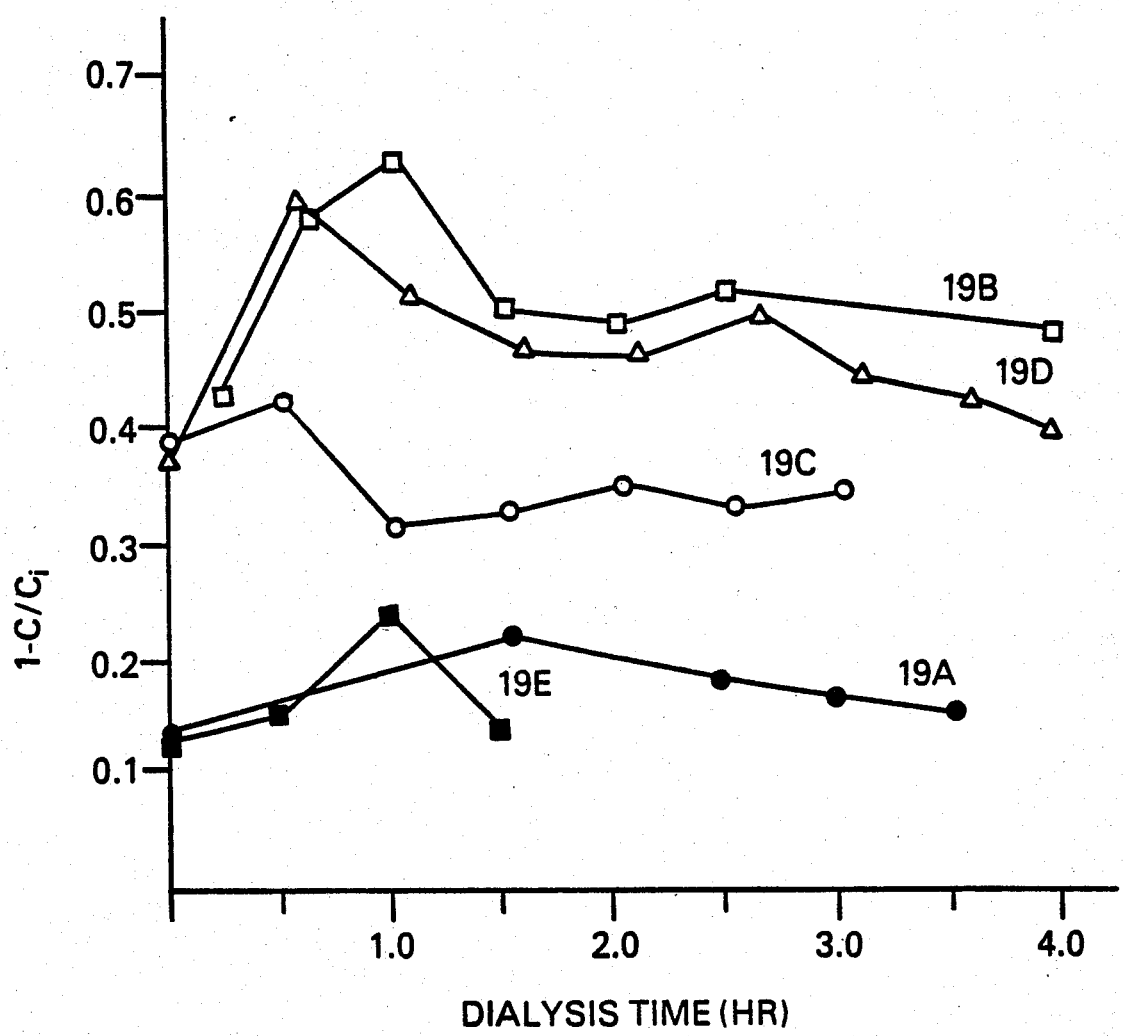

ZP - zirconium phosphate
S - soluble urease
Z.B. - zeolite-bound urease
*urease activity questionable FIG. 8b indicates the efficiency of removal of urea. With the exception of dialyzers 19A and 19E (both with little urease activity), urea efficiencies are between 30 and 60%. No evidence of urea or NH$_4^+$ saturation is seen in up to four hours of dialysis.

FIG. 8c indicates efficiency of removal of creatinine. Dialyzer 19b did not have charcoal, and thus had low efficiency of removal (and decreasing efficiency). Dialyzers 19C and 19E had slightly decreasing efficiencies (ranging from 20 to 50%) during the four hours of dialysis.

In order to determine whether the ion balances of the dialyzers were appropriate for treatment of kidney failure, the tests reported in FIGS. 9a through 9g were made.

Figure 9A:
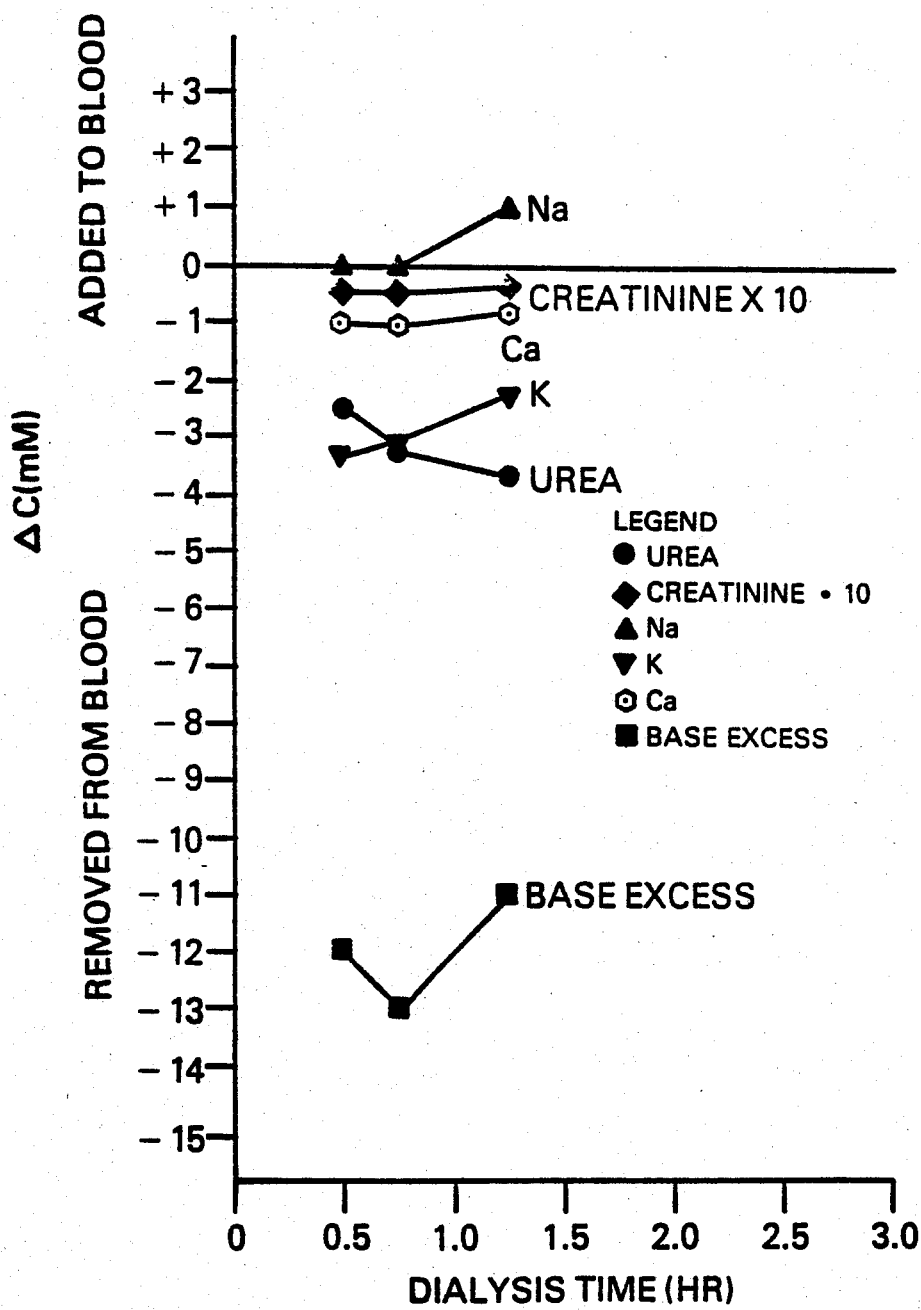

FIG. 9a indicates changes in blood ion concentration during one transit of blood through the dialyzer (inflow/outflow). In this experiment, H$^+$-Na$^+$ loaded zirconium phosphate was used in the absorbent suspension. Urea removal was adequate, but as expected, acidification of blood occurred (base excess declined). Ca$^{++}$ was also removed. Such ion changes would not be compatible with health of a uremic patient.

Figure 9B:
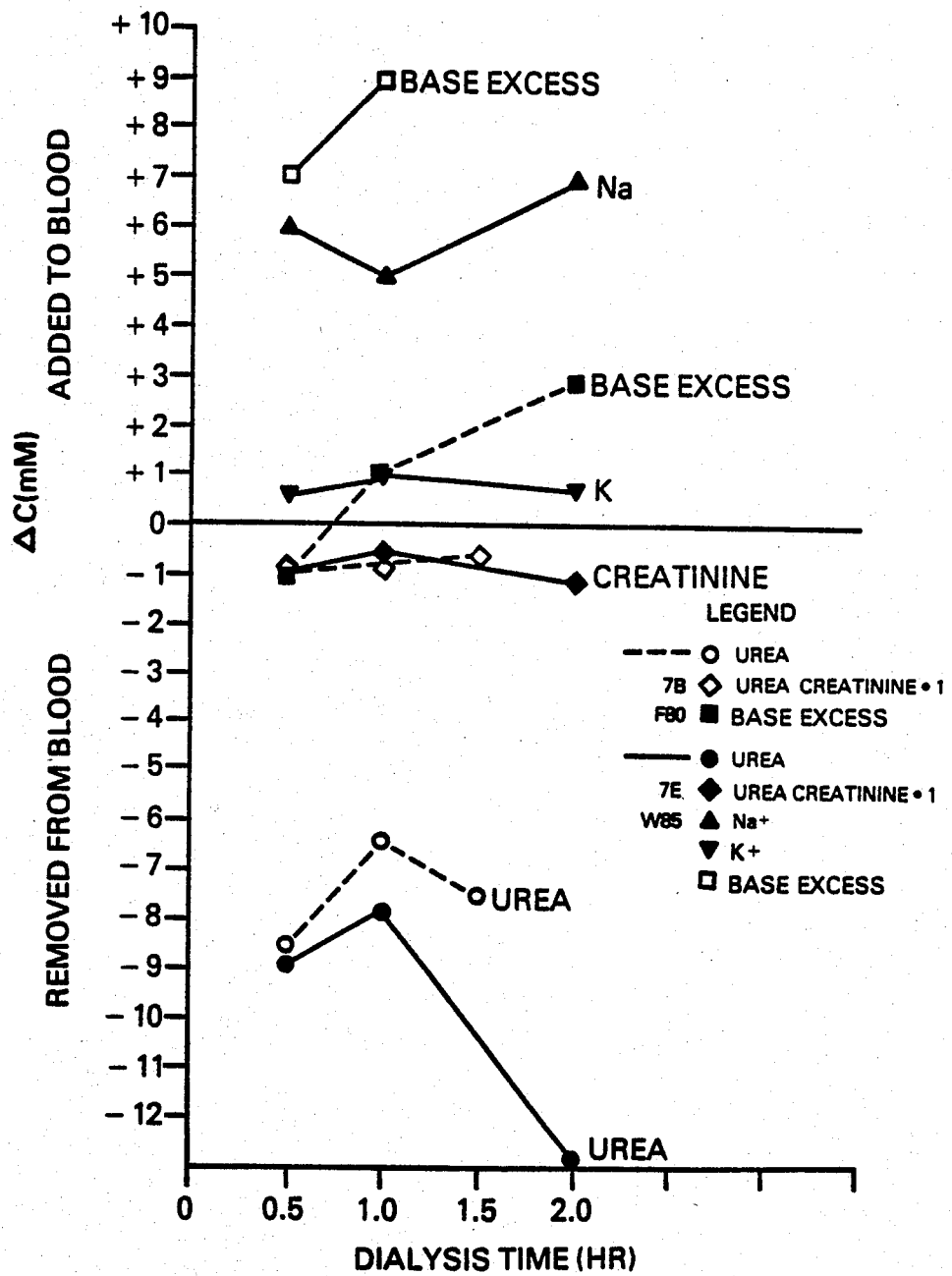

FIG. 9b represents a similar experiment but with low calcium loaded (20%) zeolite used in place of zirconium phosphate. Again, urea removal was acceptable and base return to patient was appropriate for the health of a uremic patient. However, excess (for patient health) sodium was released and returned to the blood since the predominant loading on the zeolite was Na$^+$.

FIG. 9c indicates the substance changes (inflow-outflow) during in vivo tests with the 19A dialyzer (highly calcium-loaded zeolite, and minimal urease activity). As is seen in FIG. 9c, calcium transport to blood, and sodium removal from blood, were the major ion changes. Urea removal was minimal. In addition, base removal from blood was marked, and the blood pH decreased. It is most likely that the pH change was due to calcium precipitation with bicarbonate in the dialysate. Systemic blood (inflow) sodium fell 7 mM/l. during the treatment, and blood calcium rose from 8.5 to 19.0 mg% during treatment. Arrhythmias were noted. pH fell slightly (7.35 to 7.30 pH units).

FIGS. 9d, e, f, and g refer to series 19 dialyzers, utilizing a moderately high calcium-loaded zeolite (high calcium zeolite pretreated with partial Na loadings). Inflow-outflow concentration changes are plotted vs. time for urea and various ions. In each case, Na$^+$ removal was less than with the use of the very high calcium-loaded zeolite, and became minimal by the end of the dialysis. Calcium return to the blood was also moderate, at 2-6 mM/l. change. Potassium was removed, as were urea and creatinine. Bicarbonate return was generally in proportion to level of urease activity (5-10 meq/l HCO$_3^-$). Systemic blood (inflow) changed only modestly during treatment: calcium rose 0.75-1.5 mg%, and Na decreased 1.2-3.7 meq/l.

In series 19 dialyzers with moderate Ca-loaded zeolite, calcium levels in dialysate rose from 11.5 to 22 mg% during dialysis (from 1.0 to 7.2 mg%). Sodium rose to levels of 61-96 meq/l. from 36-68 meq/l. By contrast, with highly calcium-loaded zeolites, calcium levels in dialysate rose to 91 mg% and sodium decreased to 31 meq/l.

Figure 10:
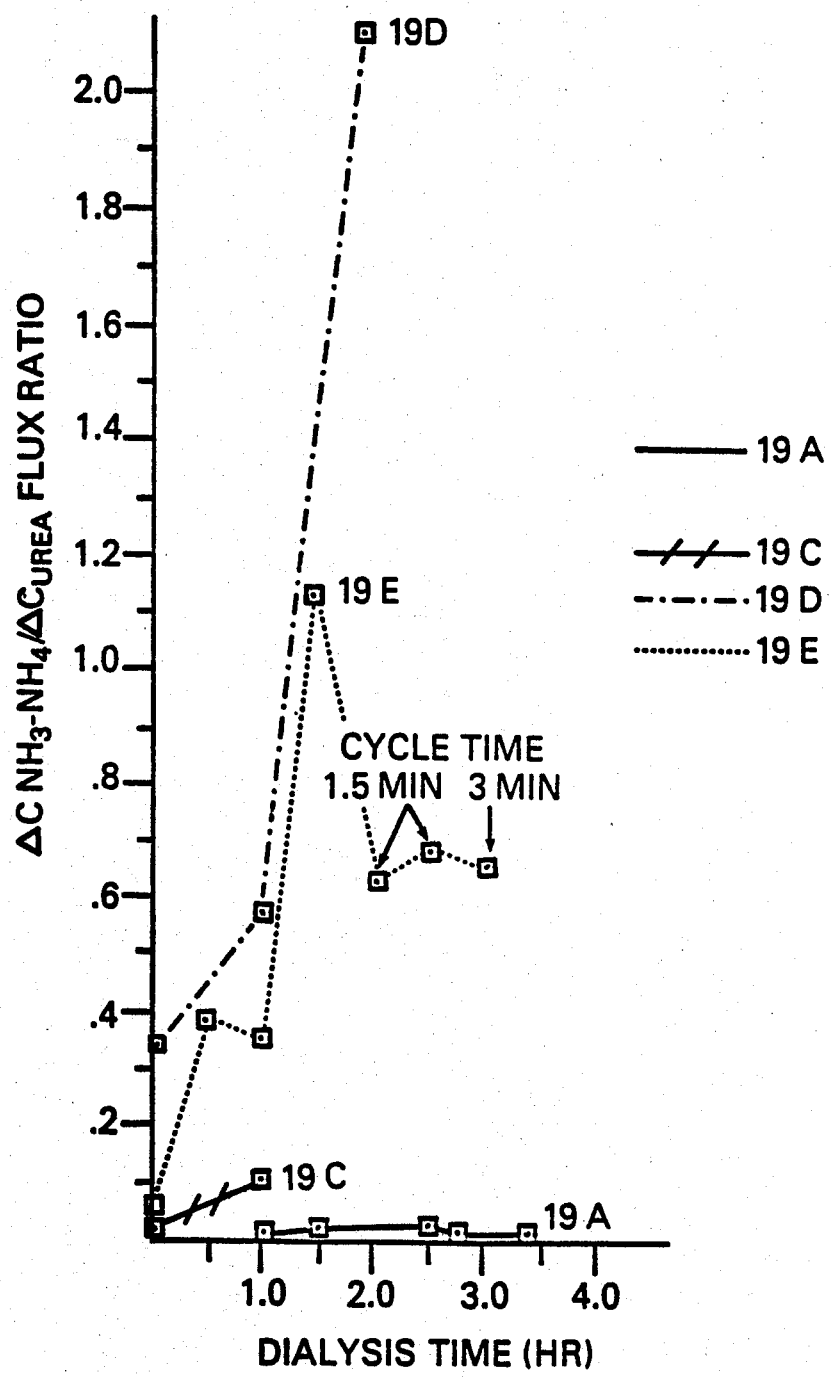

FIG. 10 indicates the ammonium generated during treatment of blood by the series 19 dialyzers. The amount of NH$_3$-NH$_4^+$ generated is divided by mM urea removed from blood, to indicate the effectiveness of NH$_4^+$ removal by zeolite. 100% return of urea nitrogen to the animal would be indicated by a $\Delta$NH$_3$-NH$_4^+$/$\Delta$urea of 2. Ammonia generation was much higher in dialyzers with higher ammonia generation (19D, E), with up to 6,000 $\mu$m/l. for E and 18,000 $\mu$M/l. for D. For 19E, longer "dwell times" for blood inside the dialyzer (1.5-3.0 minutes) results in lower NH$_4^+$ levels. Acceptable NH$_4^+$/urea ratios would be those below about 0.6 (30% urea nitrogen return as NH$_3$-NH$_4^+$). Systemic blood (inflow) ammonium levels never elevated far from normal range in any of the 19 series experiments, and no symptoms of ammonia toxicity were seen.

In each of the above dialyses, the calcium-loaded zeolite (about 40-50% Ca$^{++}$ and 50-60% Na$^+$) can be replaced by a mixture of zeolites ½-⅔ very highly Ca$^{++}$-loaded zeolite (66% Ca$^{++}$) and ⅓-½ sodium or sodium-potassium-loaded zeolite to yield a final zeolite mixture averaging about 50% Ca$^{++}$ loading.

As can be seen from the above results, reciprocating sorbent-constrained dialyzers, when operated at constant pressure, are mechanically feasible. Although relatively high flow rates are present during the start of inflow and outflow, these flows are obtainable from a venous access device such as a standard human patient fistula. Such dialyzers can be operated from venous access alone (although the flow rate in this situation is somewhat variable). The sorbent system employed is effective in removal of urea and creatinine from treated blood. In addition, in vivo and in vitro functional tests indicate lack of saturation with urea or creatinine, during repeated cycles for up to four hours, approximately 50% efficiencies being easily obtainable.

No acute toxicity was seen in any animal tests in dialysis up to three to four hours.

The dialyzers utilizing predominantly sodium-loaded zeolites caused very little change in calcium and returned bicarbonate to the animal. Moderate amounts of sodium were generated, but not enough to raise the serum sodium of the animal significantly. This return of sodium would cause problems with more efficient dialyzers in patients in renal failure.

Very highly calcium-loaded zeolites also cause problems with ion balance in the dialyzer. Dangerous hypercalcemia occurs in the animal, with levels over twice normal (in the absence of urease action). Also, in the absence of urease, significant base removal occurs due to precipitation of bicarbonate with calcium in the sorbent suspension. Significant sodium removal occurs, resulting in a 7 mM/l. decrease in serum sodium.

With moderately high calcium loading of zeolite (approximately 50% $Ca^{++}$), ion balances become appropriate for treatment of a patient in renal failure. Sodium removal diminishes during the dialysis, and is of only moderate degree. Calcium return to the animal is also moderate, and elevations of serum calcium are minimal. Base return to the patient is appropriate. Potassium is removed effectively.

Binding of urease to zeolite appears to allow effective urease activity; no apparent toxicity was associated with its use.

Liquid sterilization of the blood side compartments with Betadine ® does not affect urease activity or sorbent function and appears to be effective in preventing infection.

The peak flow rate noted in the animal tests to be up to 5 ml/sec is probably attainable from a venous access, and certainly attainable from a single catheter in a fistula. The ability to utilize venous access in this dialysis may open up alternative vascular access sites. The dialyzer filling volumes during the dialysis are stable. Ultrafiltration is as predicted by the Cuprophan ® ultrafiltration coefficient.

Use of a bicarbonate buffer in place of acetate is feasible in a self-contained (sorbent-based reciprocating) artificial kidney.

EXAMPLE 2

A second in vivo testing of the second embodiment of my novel dialysate composition and dialysate method was carried out as follows: Once again, the dialyzer utilized was the type described in U.S. Pat. No. 4,061,444. The void space of each screen, aforedescribed, as filled with absorbent mixture that contains 7 weight percent powdered activated charcoal, 20 weight percent calcium-sodium (approximately 15-50) loaded Ionsiv W (from Union Carbide), urease bound covalently thereto (20 units per ml. of sorbent suspension), 0.5% methylcellulose, and 3% glucose. Sodium bicarbonate (44 millimolar) was added and the pH adjusted to 5.5-5.8 as necessary. Carboxylic acid exchange resin in $H^+$ form is added at the rate of 10-40 grams per liter absorbent mixture.

The sorbents used in the second embodiment were prepared as follows:

Zeolite—Very Highly Calcium-Loaded

Zeolite, with half the available replacement sites filled by $Ca^{++}$ and the other half by $Na^+$, were prepared as follows: Very highly calcium-loaded zeolites (about 75% replacement sites) were obtained from Union Carbide Corporation. These very highly calcium-loaded zeolites had been prepared by forming the zeolite in a system containing a high proportion of $Ca^{++}$ (rather than $Na^+$ or $H^+$ ions). These very highly calcium-loaded zeolites contained about 4.6 meq/g of $Ca^{++}$ and about 1.5 meq/g $Na^+$. To prepare 50% $Ca^{++}$-loaded zeolite, a 75% $Ca^{++}$-loaded zeolite was filtrated with a $Na^+$ solution (hydroxide or carbonate) until the zeolite had about a 50-50 $Ca^{++}$-$Na^+$ loading.

The single zeolite contained per gram about 3.0 meq, $Ca^{++}$, about 2.5 Meq $Na^+$, and about 0.5 meq $K^+$.

Urease Bound to Calcium-Loaded Zeolite

The urease was bound to the zeolite and purified in the same manner as previously discussed in Example 1.

Aliphatic Carboxylic Acid Ion Exchanger

A second type of ion exchanger employed in this embodiment of the invention was prepared by polymerizing methacrylic acid and cross-linking the polymer thus produced with divinyl benzene. (Such resins are obtainable commercially under the trademark BIOREX-70 (Biorad Labs), ZEOCARB 226 (Permutit Co.) and AMBERLITE IRP-64 and IRP-64M (Rohm and Haas). (These latter resins are essentially anhydrous pulverized forms of IRC-50 and have been screened or sieved to give them more uniform particle size from that present in the commercial resin.) These resins are in the $H^+$ form, with IRP-64 being a 100 mesh material with 30% maximum retention on a 200 mesh screen, the remainder of the material between roughly 200-400 mesh. IRP-64N is a 325 mesh product with 90% passing that size screen. Such resins are referred to as "pharmaceutical grade" resins.

Activated Charcoal

Powdered charcoal USP was obtained from Mallinckrodt, Inc. This charcoal had been shown in vitro to adequately bind creatinine, uric acid, and other organic materials at low concentrations.

Suspending Agent

The suspending agents were the same as those used in Example 1—i.e., dextran, hydroxyethyl starch, and methylcellulose, all non-dialyzable materials. Methylcellulose was preferred, used at a concentration in the sorbent mixture in the range of 0.1-1%, usually about 0.5%. (It should be recognized that the sorbent mixtures used these examples are not in true permanent suspensions, and in time the activated charcoal and zeolites will settle out. However, the degree of suspension is sufficient to maintain a mobile sorbent mixture which by the movement of the membranes is kept in sufficient motion to continually present fresh sorbent to the dialysis membrane.) By this expedient, layering or packing of the sorbent constituents against the dialysis membrane is inhibited. Such packing slows the rate of transfer of toxins from blood as the sorbents nearest the dialysis membrane become saturated and the diffusion distance of the toxins to unsaturated sorbent increases.

Organic Buffers

An organic buffer was employed to take care of alkalosis pre-existing in the patient. Such buffers are metabolizable organic acids, e.g., acetic acid, citric acid, tartaric acid, lactic acid, and diethylmalonic acid. These acids or ions must be metabolizable since they are capable of passing through a dialysis membrane. It is preferable to use acids which have greater buffering power per unit weight, such as the acetic and diethylmalonic acids.

The dialysis was carried out using the above-described sorbent mixture and dialyzer. The sorbent in suspension was placed in a rigid case surrounding the dialyzer membrane package after the blood compartment had been injected with Betadine (PVP-iodine). Sterile irrigation fluid was rinsed into and out of the blood compartment. Several cycles were required to remove the light brown color resulting from the PVP-iodine, losing iodine by dilution and transfer across the membrane. The dialyzer blood inlet port was next attached to the AV shunt (carotid artery, jugular vein) of the mongrel dog which had been subjected to a left nephrectomy and one of whose arteries to the right kidney had been tied off. A pressure-vacuum pump was attached to a reservoir which was attached to the dialysate case. A timer controlled the pressure and vacuum on a predetermined cycle. Provision was made for sampling the inflowing and exiting blood through a rubber port by puncture with a needle. The dialysis was then started by activating the pump and continued for as long as desired.

Using the above sorbent system, there was little or no base (bicarbonate) or calcium exchange in most patients, while urea, $NH_4^+$, creatinine, etc. were effectively removed as before. However, for some patients on dialysis, bicarbonate return was still too high. In such patients, addition of an organic buffer such as lactic or diethylmalonic acid (as described above) at about 15 grams/liter of dialysate took care of the problem.

The above dialyzer with the described sorbent systems was able to effect a 50% removal of urea at a 22 g./l blood level on each cycle and creatinine at a 0.2 g./l level with a negligible calcium, sodium, or bicarbonate return (0–5 meq/l inflow-outflow difference).

The novel sorbent mixtures of the present invention have been illustrated with reference to an SSRD machine, but it is apparent that it would be equally useful in a hollow filter dialyzer or in peritoneal dialysis with a system to cycle peritoneal dialysate into and out of the abdomen.

What is claimed is:

1. A composition for use in dialysis comprising a surface adsorptive substance capable of adsorption of uremic substances, water, a suspending agent, urease, a calcium-loaded cation exchanger, an aliphatic carboxylic acid resin in the $H^+$ form, and a metabolizable organic acid buffer.

2. A composition according to claim 1 in which the metabolizable organic acid is diethylmalonic acid.

3. A composition according to claim 1 in which the aliphatic carboxylic acid resin is polymerized methacrylic acid cross-linked with divinylbenzene.

4. A composition according to claim 1 in which the cation exchanger is a calcium-loaded zeolite.

5. The composition of claim 4 in which the zeolite is about 50% calcium loaded.

6. A composition according to claim 1 in which the cation exchanger is a mixture of zeolites capable of furnishing from 2.8–3.2 meq. of calcium ions per gram.

7. A composition according to claim 1 in which the suspending agent is methylcellulose.

8. A composition according to claim 1 in which the surface adsorptive substance is activated charcoal.

9. A composition according to claim 1 in which the total weight of solids in the suspension is not more than 3 g/l.

10. A composition according to claim 1 in which the cation exchanger is a zeolite or mixture of zeolites and the urease is bound to a portion of one of the zeolites.

* * * * *